(12) United States Patent
Tønnesen et al.

(10) Patent No.: US 10,111,842 B2
(45) Date of Patent: Oct. 30, 2018

(54) EUTECTIC SOLVENTS AND USES THEREOF

(71) Applicant: UNIVERSITY OF OSLO, Oslo (NO)

(72) Inventors: Hanne Hjorth Tønnesen, Oslo (NO); Kristine Opsvik Wikene, Oslo (NO)

(73) Assignee: University of Oslo, Oslo (NO)

( * ) Notice: Subject to any disclaimer, the term of this patent is extended or adjusted under 35 U.S.C. 154(b) by 0 days.

(21) Appl. No.: 15/540,688

(22) PCT Filed: Dec. 30, 2015

(86) PCT No.: PCT/IB2015/002554
§ 371 (c)(1),
(2) Date: Jun. 29, 2017

(87) PCT Pub. No.: WO2016/108083
PCT Pub. Date: Jul. 7, 2016

(65) Prior Publication Data
US 2018/0000753 A1    Jan. 4, 2018

Related U.S. Application Data

(60) Provisional application No. 62/098,463, filed on Dec. 31, 2014.

(51) Int. Cl.
| | | |
|---|---|---|
| *A61K 31/14* | (2006.01) |
| *A61K 31/409* | (2006.01) |
| *A61K 31/20* | (2006.01) |
| *A61K 31/661* | (2006.01) |
| *A01N 31/12* | (2006.01) |
| *A01N 37/36* | (2006.01) |
| *A01N 43/16* | (2006.01) |
| *A01N 33/12* | (2006.01) |
| *A61K 31/047* | (2006.01) |

(52) U.S. Cl.
CPC .............. *A61K 31/14* (2013.01); *A01N 33/12* (2013.01); *A01N 37/36* (2013.01); *A01N 43/16* (2013.01); *A61K 31/20* (2013.01); *A61K 31/409* (2013.01); *A61K 31/661* (2013.01); *A61K 31/047* (2013.01); *H05K 999/99* (2013.01)

(58) Field of Classification Search
None
See application file for complete search history.

(56) References Cited

U.S. PATENT DOCUMENTS 6,573,258 B2 *  6/2003  Bommer .............. A61K 31/409
514/185

FOREIGN PATENT DOCUMENTS

WO    WO 2014/131906 A1 *  9/2014  .............. A01N 1/02

* cited by examiner

*Primary Examiner* — Brian J Davis
(74) *Attorney, Agent, or Firm* — Casmir Jones S.C.; J. Mitchell Jones

(57) ABSTRACT

Provided herein are photosensitizer compounds for use in a variety of clinical, industrial, and research applications. In particular, provided are deep eutectic solvents and natural deep eutectic solvents for use in killing of bacteria.

19 Claims, 9 Drawing Sheets

EUTECTIC SOLVENTS AND USES THEREOF

FIELD OF INVENTION

Provided herein are photosensitizer compounds for use in a variety of clinical, industrial, and research applications. In particular, provided are deep eutectic solvents and natural deep eutectic solvents for use in killing of microorganisms (e.g., bacteria and/or fungi).

BACKGROUND

Antibacterial photodynamic therapy (aPDT) is a treatment for bacterial infections. Systemic side effects may be greatly reduced and the bacteria specifically targeted without the immediate risk of inducing bacterial resistance (Hamblin M R, et al., *Photochem Photobiol Sci* 2004; 3: 436-450; Ikai H, et al., *PloS one* 2013; 8: e81316). aPDT utilizes a combination of visible light, a photosensitizer (PS) and oxygen to produce cytotoxic species.

Porphyrins are aromatic heterocyclic compounds that are ubiquitous in nature, and have been widely investigated in photodynamic therapy of tumours and microbial infections (Almeida A, et al., *Compr Ser Photoch* 2011; 11: 83-160; O'Connor A E, et al., *Photochem Photobiol* 2009; 85: 1053-1074; Mang T S, et al., *Lasers Surg Med* 2012; 44: 588-596; Berenbaum M, et al., *Br J Cancer* 1986; 54: 717; Nitzan Y, et al., *Photochem Photobiol* 1992; 55: 89-96; Karunakaran S C, et al., *ACS Chem Biol* 2013; 8: 127-132; Prasanth C S, et al., *Photochem Photobiol* 2014; 90: 628-640; Banfi S, et al., *J Photochem Photobiol B: Biol* 2006; 85: 28-38).

In cancer treatment neutral and negatively charged porphyrins (e.g., porfimer sodium) and the related chlorins (e.g. meso-tetrahydroxyphenylchlorin) have been studied as effective treatment modalities (O'Connor et al., supra). However, in aPDT there is a general agreement that positively charged groups on the porphyrin is important for antibacterial photodynamic effect (Prasanth et al., supra; Banfi et al., supra; Stojiljkovic I, et al., *Expert Opin Invest Drugs* 2001; 10: 309-320; Merchat M, et al., *J Photochem Photobiol B: Biol* 1996; 35: 149-157). This understanding reasons in the outer wall and cytoplasmic membrane structure of Gram-positive and Gram-negative bacteria. The Gram-positive bacteria outer wall consists of a porous peptidoglycan layer with traversing lipoteichoic acids where even 30 000-60 000 Da peptides may diffuse through (Friedrich C L, et al., *Antimicrob Agents Chemother* 2000; 44: 2086-2092). The Gram-negative bacteria outer structure contains an additional highly organized outer lipid bilayer membrane composed of negatively charged lipopolysaccharides, polysaccharides, proteins and lipoproteins (Maisch T, et al., *Photochem Photobiol Sci* 2004; 3: 907). This structure usually renders the bacteria resistant to negatively charged or neutral porphyrins which efficiently photoinactivate Gram-positive bacteria (Hamblin et al., supra; Nitzan et al., supra; Maisch T, et al., supra; Malik Z, et al., *J Photochem Photobiol B: Biol* 1990; 5: 281-293).

Previous formulations of porphyrins have mostly been based on simple preparations in water, liposomes and DMSO (Banfi et al., supra; Merchat et al, supra; Tang H M, et al., *J Inf Chemother* 2007; 13: 87-91). Particularly for the neutral porphyrins, these preparations have been inefficient in photoinactivation of Gram-negative bacteria. In aPDT it is advantageous to use water miscible formulations as the PS needs to penetrate aqueous exudate or other body fluids to reach the target bacteria. Also the bacterial outer cover is largely hydrophilic and will not allow close interactions with hydrophobic compounds (Malik Z, et al., *J Photochem Photobiol B: Biol* 1992; 14: 262-266). A neutral, hydrophobic PS incorporated in liposomes will therefore not readily be released from the carrier and interact with the bacterial membrane (Merchat et al., supra; Haukvik T, et al., *Pharmazie* 2009; 64: 666-673).

Additional formulations are needed to aid in inactivation of bacteria and other microorganisms.

SUMMARY

Provided herein are photosensitizer compounds for use in a variety of clinical, industrial, and research applications. In particular, provided are deep eutectic solvents and natural deep eutectic solvents for use in killing of microorganisms (e.g., bacteria and/or fungi).

For example, in some embodiments, the present disclosure provides methods of killing or inhibiting the growth of a cell (e.g., bacterial cell, fungal cell, or cancer cell), comprising: contacting the cell with a eutectic solvent under conditions such that the eutectic solvent kills or inhibits the growth of the cell. In some embodiments, the eutectic solvent is a deep eutectic solvent (DES) or a natural deep eutectic solvent (NADES). In some embodiments, the eutectic solvent comprises at least three components (e.g., at least two components). In some embodiments, the components are selected from, for example, an organic acid, a salt, a sugar, a sugar alcohol, an amino acid, a di or tri alkanol, and a choline derivative. In some embodiments, the choline derivative is choline or phosphatidyl choline. In some embodiments, the sugar or sugar alcohol is, for example, sucrose, glucose, fructose, lactose, maltose, cellobiose, arabinose, ribose, ribulose, galactose, rhamnose, raffinose, xylose, sucrose, mannose, trehalose, mannitol, sorbitol, inositol, ribitol, galactitol, erythritol, xylitol and adonitol, or a phosphate thereof. In some embodiments, the organic acid is, for example, malic acid, maleic acid, citric acid, lactic acid, pyruvic acid, fumaric acid, succinic acid, lactic acid, acetic acid, aconitic acid, tartaric acid, malonic acid, ascorbic acid, glucuronic acid, oxalic acid, neuraminic acid or sialic acids. In some exemplary embodiments, one component is citric acid, choline chloride, D-(+)-glucose, or sucrose and the other component is sucrose, D-(+)-trehalose, choline chloride, DL-malic acid, glycerol, sucrose, and D-(−)-fructose. In some embodiments, first and second component are present at a molar ratio of 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, or 5:4.

In some embodiments, the eutectic solvent comprises an organic acid and a sugar or sugar alcohol in a molar ratio characteristic of formation of eutectic solution by the organic acid and a sugar or sugar alcohol. In some embodiments, the eutectic solvent comprises a choline salt and a sugar, sugar alcohol, or organic acid in a molar ratio consistent with formation of eutectic solution by the organic acid and a sugar or sugar alcohol. In some embodiments, the eutectic solvent comprises at least two sugars or sugar alcohols in a molar ratio consistent with formation of eutectic solution by the at least two sugars or sugar alcohols. In some embodiments, the eutectic solvent comprises at least three sugars or sugar alcohols or organic acids in a molar ratio consistent with formation of eutectic solution by the at least two sugars or sugar alcohols.

In some exemplary embodiments, the eutectic solvent is citric acid and sucrose at a molar ratio of 1:1, choline chloride and maleic acid at a molar ratio of 1:1, choline chloride and glycerol at a molar ration of 1:1, D-(+)-glucose and DL-malic acid at a molar ratio of 1:1, choline chloride and citric acid at a molar ratio of 2:1, citric acid and xylitol at a molar ratio of 1:1, choline chloride and xylitol at a molar ratio of 5:2, choline chloride and D-(−)-fructose at a molar ratio of 5:2, choline chloride and maleic acid 2:1, choline chloride and maleic acid 1:3, or glucose and sucrose 1:1. In some embodiments, the eutectic solvent comprises sucrose, glucose, and fructose at a ratio of 1:1:1. In some embodiments, the eutectic solvent comprises DL-malic acid and D-(−)-fructose and D-(+)-glucose at a molar ratio 1:1:1. In some embodiments, the eutectic solvent is provided in a solution comprising a 1:1 to 1:1000 (e.g., 1:20 to 1:1000, 1:50 to 1:500, or 1:00 to 1:250) dilution of said eutectic solvent in water or an aqueous buffer.

In some embodiments, the eutectic solvent further comprises a photosensitizer. In some embodiments, the photosensitizer is, for example, porphyrins, chlorins, bacteriochlorins, phthalocyanines, texaphyrins, sapphyrins, porphycene derivatives, curcuminoids, flavins, or derivatives thereof. In some embodiments, the porphyrin is 55,10,15,20-tetrakis(4-hydroxyphenyl)porphyrin (THPP), tetra-(4-trimethylanilinum)-porphine tetrachloride (TMAP), or porphyrin tetra-(4-carboxyphenyl)-porphine (TCPP) and the curcuminoid is curcumin.

In some embodiments, the bacteria are Gram negative bacteria or Gram positive bacteria (e.g., *E. faecalis, E. coli* or *S. aureus*) and the fungi are yeast (e.g., *Candida*). In some embodiments, the method further comprises the step of contacting the eutectic solvent and the bacteria or fungi with a light source.

Additional embodiments provide the use of a eutectic solvent in the killing or inhibition of growth of a cell (e.g., bacterial cell, fungal cell, or cancer cell).

Yet other embodiments provide a composition or kit comprising a eutectic solvent and a photosensitizer.

In still further embodiments, a system comprising the composition and a light source is provided.

Additional embodiments are described herein.

DEFINITIONS

Figure 1:
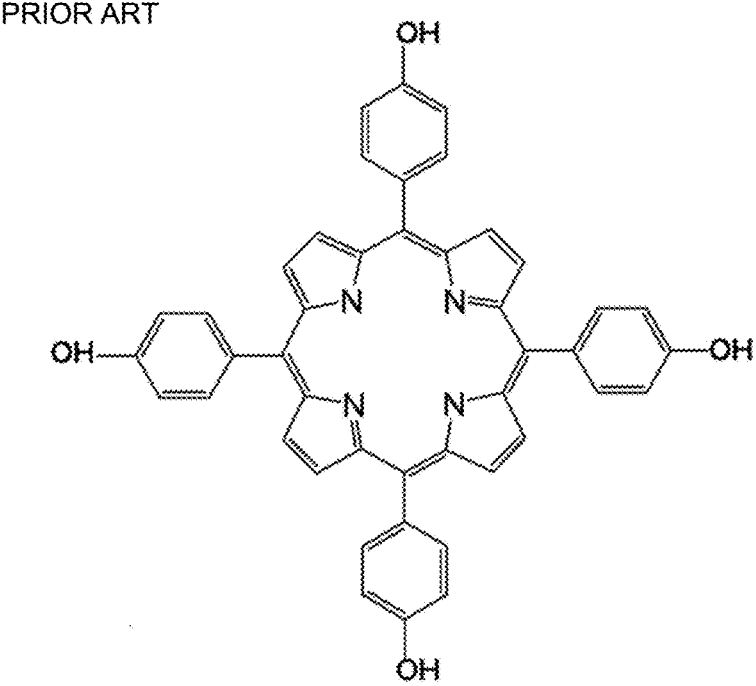
FIG. 1 shows the molecular structure of THPP.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, the term "eutectic system" describes a homogeneous solid mix of atomic and/or chemical species, to form a joint super-lattice, by striking a defined atomic percentage ratio or molar ratio between the components. It is only in the defined atomic/molar ratio that the eutectic system melts as a whole, at a specific temperature (the eutectic temperature). The eutectic temperature is the lowest possible melting temperature over all of the mixing ratios for the involved component species.

As used herein, the term "Natural Deep Eutectic Solvents (NADES)" refers to deep eutectic solvents and ionic liquids which are composed of two or more natural compounds that are present at high concentrations in all living cells and that form a eutectic system, e.g., organic acids, sugars, alcohols, amines and amino acids.

The term "two or more components" when used in reference to a NADES refers to a pair or more compounds that form a NADES when mixed at the appropriate molar ratio.

The term "three or more components" when used in reference to a NADES refers to a three or more compounds that form a NADES when mixed at the appropriate molar ratio.

The term "molar ratio characteristic of formation of a eutectic solution" refers to the molar ratio at which two given compounds known to form a eutectic system form a eutectic solution.

As used herein, the term "active" as applied to a composition, extract, substance, mixture, solid, liquid, etc., refers to having the ability to modulate (e.g., alter) biological activity or cell growth.

A "subject" is an animal, such as a vertebrate, and preferably a mammal, such as a human. Mammals are understood to include, but are not limited to, murines, simians, humans, bovines, cervids, equines, porcines, canines, felines, etc.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "subject" refers to individuals (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment for a condition characterized by the presence of biofilm-forming bacteria, or in anticipation of possible exposure to biofilm-forming bacteria.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "virulence" refers to the degree of pathogenicity of a microorganism (e.g., bacteria or fungus), e.g., as indicated by the severity of the disease produced or its ability to invade the tissues of a subject. It is generally measured experimentally by the median lethal dose ($LD_{50}$) or median infective dose ($ID_{50}$). The term may also be used to refer to the competence of any infectious agent to produce pathologic effects.

As used herein, the term "effective amount" refers to the amount of a composition (e.g., a eutectic solvent) sufficient to effect beneficial or desired results. An effective amount can be administered in one or more administrations, applications or dosages and is not intended to be limited to a particular formulation or administration route.

As used herein, the term "administration" refers to the act of giving a drug, prodrug, or other agent, or therapeutic treatment (e.g., eutectic solvent) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, by injection (e.g., intravenously, subcutaneously, intratumorally, intraperitoneally, etc.), topical administration and the like.

As used herein, the term "co-administration" refers to the administration of at least two agent(s) (e.g., eutectic solvent in combination with an antimicrobial agent, antifungal agent, or chemotherapeutic agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "wound" refers broadly to injuries to tissue including the skin, subcutaneous tissue, muscle, bone, and other structures initiated in different ways, for example, surgery, (e.g., open post cancer resection wounds, including but not limited to, removal of melanoma and breast cancer etc.), contained post-operative surgical wounds, pressure sores (e.g., from extended bed rest) and wounds induced by trauma. As used herein, the term "wound" is used without limitation to the cause of the wound, be it a physical cause such as bodily positioning as in bed sores or impact as with trauma or a biological cause such as disease process, aging process, obstetric process, or any other manner of biological process. Wounds caused by pressure may also be classified into one of four grades depending on the depth of the wound: i) Grade I: wounds limited to the epidermis; ii) Grade II: wounds extending into the dermis; iii) Grade III: wounds extending into the subcutaneous tissue; and iv) Grade IV: wounds wherein bones are exposed (e.g., a bony pressure point such as the greater trochanter or the sacrum). The term "partial thickness wound" refers to wounds that are limited to the epidermis and dermis; a wound of any etiology may be partial thickness. The term "full thickness wound" is meant to include wounds that extend through the dermis.

As used herein, "wound site" refers broadly to the anatomical location of a wound, without limitation.

As used herein, the term "dressing" refers broadly to any material applied to a wound for protection, absorbance, drainage, treatment, etc. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer) (Kannon and Garrett (1995) *Dermatol. Surg.* 21: 583-590; Davies (1983) *Burns* 10: 94; each herein incorporated by reference). The present invention also contemplates the use of dressings impregnated with pharmacological compounds (e.g., antibiotics, antiseptics, thrombin, analgesic compounds, etc). Cellular wound dressings include commercially available materials such as Apligraf®, Dermagraft®, Biobrane®, TransCyte®, Integra® Dermal Regeneration Template®, and OrCell®.

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., photosensitizer in) with a carrier, inert or active (e.g., eutectic solvent), making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintregrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). In certain embodiments, the compositions of the present invention may be formulated for veterinary, horticultural or agricultural use. Such formulations include dips, sprays, seed dressings, stem injections, sprays, and mists. In certain embodiments, compositions of the present invention may be used in any application where it is desirable to alter (e.g., inhibit) the formation of biofilms, e.g., food industry applications; consumer goods (e.g., medical goods, goods intended for consumers with impaired or developing immune systems (e.g., infants, children, elderly, consumers suffering from disease or at risk from disease), and the like.

As used herein, the term "medical devices" includes any material or device that is used on, in, or through a subject's or patient's body, for example, in the course of medical treatment (e.g., for a disease or injury). Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, needles, drug delivery skin patches, drug delivery mucosal patches and medical sponges. Body cavity and personal protection devices, include, but are not limited to, tampons, sponges, surgical and examination gloves, contact lenses, and toothbrushes. Birth control devices include, but are not limited to, intrauterine devices (IUDs), diaphragms, and condoms.

As used herein, the term "therapeutic agent," refers to compositions that decrease the infectivity, morbidity, or onset of mortality in a subject (e.g., a subject contacted by a biofilm-forming microorganism) or that prevents infectivity, morbidity, or onset of mortality in a host contacted by a biofilm-forming microorganism. As used herein, therapeutic agents encompass agents used prophylactically. Such agents may additionally comprise pharmaceutically acceptable compounds (e.g., adjuvants, excipients, stabilizers, diluents, and the like). In some embodiments, the therapeutic agents of the present invention are administered in the form of topical compositions, injectable compositions, ingestible compositions, and the like. When the route is topical, the form may be, for example, a solution, cream, ointment, salve or spray.

As used herein, the term "pathogen" refers to a biological agent that causes a disease state (e.g., infection, cancer, etc.) in a host. "Pathogens" include, but are not limited to, viruses, bacteria, archaea, fungi, protozoans, *mycoplasma*, prions, and parasitic organisms.

As used herein, the term "microbe" refers to a microorganism and is intended to encompass both an individual organism, or a preparation comprising any number of the organisms.

As used herein, the term "microorganism" refers to any species or type of microorganism, including but not limited to, bacteria, archaea, fungi, protozoans, *mycoplasma*, and parasitic organisms.

As used herein, the term "fungi" is used in reference to eukaryotic organisms such as the molds and yeasts, including dimorphic fungi.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces,* and *Rickettsia*. All forms of bacteria are included within this definition including cocci, bacilli, spirochetes, spheroplasts, protoplasts, etc. Also included within this term are prokaryotic organisms that are Gram-negative or Gram-positive. "Gram-negative" and "Gram-positive" refer to staining patterns with the Gram-staining process, which is well known in the art. (See e.g., Finegold and Martin, Diagnostic Microbiology, 6th Ed., CV Mosby St. Louis, pp. 13-15 (1982)). "Gram-positive bacteria" are bacteria that retain the primary dye used in the Gram-stain, causing the stained cells to generally appear dark blue to purple under the microscope. "Gram-negative bacteria" do not retain the primary dye used in the Gram-stain, but are stained by the counterstain. Thus, Gram-negative bacteria generally appear red.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "cell culture" refers to any in vitro culture of cells, including, e.g., prokaryotic cells and eukaryotic cells. Included within this term are continuous cell lines (e.g., with an immortal phenotype), primary cell cultures, transformed cell lines, finite cell lines (e.g., non-transformed cells), bacterial cultures in or on solid or liquid media, and any other cell population maintained in vitro.

As used herein, the term "antimicrobial agent" refers to composition that decreases, prevents or inhibits the growth of bacterial and/or fungal organisms. Examples of antimicrobial agents include, e.g., antibiotics and antiseptics.

The term "antiseptic" as used herein is defined as an antimicrobial substance that inhibits the action of microorganisms, including but not limited to α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts. One skilled in the art is cognizant that these antiseptics can be used in combinations of two or more to obtain a synergistic or additive effect. Some examples of combinations of antiseptics include a mixture of chlorhexidine, chlorhexidine and chloroxylenol, chlorhexidine and methylisothiazolone, chlorhexidine and (α-terpineol, methylisothiazolone and α-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms, preferably without damage to the host. For example, the antibiotic may inhibit cell wall synthesis, protein synthesis, nucleic acid synthesis, or alter cell membrane function.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

DETAILED DESCRIPTION

Provided herein are photosensitizer compounds for use in a variety of clinical, industrial, and research applications. In particular, provided are deep eutectic solvents and natural deep eutectic solvents for use in killing of microorganisms (e.g., bacteria and/or fungi).

Natural deep eutectic solvents (NADES) are a third type of liquid, separate from water and lipids, which are present in all living cells. NADES include natural compounds that are omnipresent in nature, such as amino acids, sugars and simple organic acids. These eutectic solvents find use in drug delivery as they are non-toxic, environmentally friendly, sustainable, cheap, and have unique solubilising properties. Described herein is the use of NADES and deep eutectic solvents (DES) as solvents for photosensitizers in photodynamic therapy (PDT) of, for example, bacterial infections (aPDT), fungal infections, and cancer treatment. At certain concentrations NADES also possess antibacterial properties in the absence of a photosensitizer, and a synergistic effect between the photosensitizer and NADES is observed. By application of NADES (See e.g., Experimental section below) it was demonstrated that a strongly hydrophobic photosensitizer which was non-active under biological conditions became highly water soluble and caused 100% eradication of both Gram positive and Gram negative bacteria at a nano-molar concentration. Commonly used aPDT photosensitizers are cationic as neutral compounds are regarded inefficient. The results demonstrated that neutral, anionic, and cationic photosensitizers are efficient when incorporated in NADES. Both water soluble and insoluble photosensitizers are soluble in specific NADES, thus the selection of applicable photosensitizers in PDT can be largely increased compared to present formulation approaches which often include use of organic solvents (e.g., DMSO). Further, the concentration of photosensitizer in the preparations can be strongly reduced, reducing side effects, increasing compliance, and providing economic and environmental benefits.

Provided herein is a low- to medium viscous homogenous solution of a photosensitizer. It is possible to add enzymes, peptides/proteins or other components that e.g., enhance the phototoxic effect, facilitate wound healing or induce cytotoxicity. The solution may be sprayed, brushed or dripped on a topical infected area, or incorporated in a wound dressing (similar to honey dressings). Solid foams (e.g., alginate foams) may be suitable vehicles for integration of the NADES solution to form a wound dressing. The solutions may also be injected directly into a tumor (intra tumoral administration) or formulated as encapsulated nanoparticles that are injected into the blood stream, selectively target tumor tissue and release the photosensitizer dissolved in NADES at the tumor site. In some embodiments, following administration, radiation of the proper wavelength (depending on the NADES and photosensitizer) is applied on the affected area by application of e.g., optical fibers. The formulation thereby generates cytotoxic species that eradicate bacteria and/or tumor cells.

Multiple NADES were developed during the course of development of embodiments of the present invention. The liquids obtained were of various viscosities with melting points well below room temperature. Any water remaining in the solution is tightly bound in the eutectic structure. Results demonstrated that NADES dissolve photosensitizers with porphyrin and diarylheptanoid structures. These photosensitizers are not water soluble, but can be dissolved in concentrations up to mg/ml in NADES. The photosensitizers were kept in solution for several weeks upon dilution 200 times in water, which demonstrated that the solubilising structures of the NADES were preserved and could withstand extensive dilution. This is beneficial with respect to the formulation of parenteral products which should be prepared as isotonic, aqueous solutions of low viscosity.

Selected NADES were highly toxic to multiple bacteria (See e.g., Experimental Section below) (completely inactivated the bacteria) without irradiation. Some NADES that were less dark toxic were phototoxic to the same bacteria when irradiated with low doses of UVA. Upon dissolution of the photosensitizers in the selected NADES and dilution of the NADES 100 times in phosphate buffered saline to eliminate the toxic effect from the NADES, a phototoxic effect was induced by the photosensitizers. A synergistic antibacterial effect was observed by application of less diluted (50 times) NADES-photosensitizer preparations on E. faecalis and E. coli. It was found that selected NADES could be diluted up to approximately 50 times in phosphate buffered saline and still be highly toxic to the bacteria, both with and without irradiation. Compared to traditional antibiotics, photosensitizers in antibacterial PDT produce free radicals and toxic species that attack the bacteria in a non-specific manner which lowers the risk of developing resistant bacteria. The advantage of PDT in cancer treatment is the selective localization of the photosensitizer at the tumor site, and the non-specific destruction of the cancerous cells without the widespread side-effects known to follow conventional cancer treatment.

The composition of certain NADES is quite similar to honey, except for certain trace compounds. Honey is currently used in treatment of persistent wound infections. The advantage of NADES compared to honey is that the composition of NADES is simple, standardized, and easy to produce in large volumes without batch to batch variations. The enzyme glucose oxidase has been identified as the major antibacterial component of honey. Enzymes are demonstrated to be soluble in NADES with preservation of enzymatic effect, and glucose oxidase can therefore be added to the samples.

In topical antibacterial treatment today most clinicians use traditional antibiotics like penicillin, polypeptides and macrolide antibiotics, both for oral administration, intravenous and topical administration. Silver dressings like Allevyn*Ag is available for prevention of infection and supplementary treatment of established bacterial infections. Products containing honey like MediHoney Antibacterial Medical Honey cream, gel and dressing are available in several countries. For photodynamic treatment of oral infections, Periowave™ utilizes the photosensitizer methylene blue and is approved in Canada, the European Union, United Kingdom and is under review by the US FDA.

In cancer treatment, surgery, radiation and chemotherapy, alone or in combination, are the most common treatment options. In PDT of cancer and precancerous conditions, Photofrin®, Levulan® and Metvix® are available. Photofrin® is a simple freeze dried powder of porfimer sodium that is dissolved before injection and approved for the treatment of cancer of the esophagus, Barrett esophagus and endobronchial cancer. Levulan® is a solution of aminolevulinic acid (ALA) and Metvix® a cream containing the methyl ester of ALA for topical treatment of actinic keratosis. Another water soluble photosensitizer, a porphyrin, developed by PCI Biotech is currently in clinical studies for head and neck cancer and bile duct cancer.

Thus, embodiments of the present disclosure provide eutectic solvents for use in a variety of research, clinical, therapeutic, and screening applications. These compositions and methods provide improved methods of killing bacteria (e.g. in wounds) and delivering toxic payloads (e.g., to tumors).

I. Solvents

In some embodiments, eutectic solvents are mixtures of materials of natural origin, or are based on mixtures of at least two (e.g., at least three) compounds, substantially without chemical or ionic bonding. One component of the solvents is preferably selected from at least one naturally occurring organic acid or an inorganic compound, such as a salt. Another component is preferably selected from at least one naturally occurring mono- or dimeric sugar, sugar alcohol, amino acid, di or tri alkanol or choline derivatives, such as choline or phosphatidyl choline. The sugar or sugar alcohol may be selected from the group of, for example, sucrose, glucose, fructose, lactose, maltose, cellobiose, arabinose, ribose, ribulose, galactose, rhamnose, raffinose, xylose, sucrose, mannose, trehalose, mannitol, sorbitol, inositol, ribitol, galactitol, erythritol, xylitol and adonitol, and, as well as their phosphates. The organic acid may be selected from malic acid, maleic acid, citric acid, lactic acid, pyruvic acid, fumaric acid, succinic acid, lactic acid, acetic acid, aconitic acid, tartaric acid, malonic acid, ascorbic acid, glucuronic acid, oxalic acid, neuraminic acid and sialic acids (See e.g., WO 2011/155829; herein incorporated by reference in its entirety) In certain solvents additionally further components may be present, such as water, phenolics, etc. These additional compounds are generally present in minor amounts, such as below 5 wt. %. Suitable examples of inorganic compounds are the phosphates, sulfates, sulfites and halogenides, such as, for example, $NaH_2PO_4$, $Na_2HPO_4$, $NaHSO_3$, $Na_2SO_4$, CaCb, MgCb, KCl, NaCl and KI.

In some preferred embodiments, the eutectic solvents and NADES of embodiments of the present invention comprise a mixture of purified or pharmaceutical grade components of the eutectic solvent. For example, the components (e.g., organic acid, sugar, sugar alcohol, choline derivative, etc.) are preferably at least 95%, 96%, 97%, 98%, 99% or 99.5% pure. In some embodiments, the solvents and NADES of embodiments of the present invention are specifically not a naturally occurring or produced NADES, for example honey.

Specific examples of eutectic solvents are described in the Experimental section. For example, in some embodiments, the first component is, for example, citric acid, choline chloride, D-(+)-glucose, or sucrose and the second component is, for example, sucrose, D-(+)-trehalose, choline chloride, DL-malic acid, glycerol, sucrose, or D-(-)-fructose. In some embodiments, the first and second component are present at a molar ratio of approximately 1:1 to 5:1 or the inverse (e.g., 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, or 5:4, etc., see Tables in the examples for ratios of specific components), although other ratios are specifically contemplated. For example, in some embodiments, the eutectic solvent comprises an organic acid and a sugar or sugar alcohol in a molar ratio characteristic of formation of eutectic solution by said organic acid and a sugar or sugar alcohol; in some embodiments, the eutectic solvent comprises a choline salt and a sugar, sugar alcohol, or organic acid in a molar ratio consistent with formation of eutectic solution by said organic acid and a sugar or sugar alcohol; in some embodiments, the eutectic solvent comprises at least two sugars or sugar alcohols in a molar ratio consistent with formation of eutectic solution by said at least two sugars or sugar alcohols; and in some embodiments, the eutectic solvent comprises at least three sugars or sugar alcohols or organic acids in a molar ratio consistent with formation of eutectic solution by said at least two sugars or sugar alcohols.

In some particular embodiments, the eutectic solvent is, for example, citric acid and sucrose at a molar ratio of 1:1, choline chloride and maleic acid at a molar ratio of 1:1, choline chloride and glycerol at a molar ration of 1:1, or D-(+)-glucose and DL-malic acid at a molar ratio of 1:1. In some embodiments, the eutectic solvent further comprises a photosensitizer. The present disclosure is not limited to particular photosensitizers. Examples include, but are not limited to, a porphyrin (e.g., 55,10,15,20-tetrakis(4-hydroxyphenyl)porphyrin (THPP), tetra-(4-trimethylanilinum)-porphine tetrachloride (TMAP), or porphyrin tetra-(4-carboxyphenyl)-porphine (TCPP)), a phthalocyanine, a chlorin, a curcuminoid (e.g., curcumin), a flavin, or derivatives thereof.

In some embodiments, the eutectic solvent and/or photosensitizer are provided in a solution comprising a 1:1, 1:20 to 1:1000 dilution of said eutectic solvent in water or an aqueous buffer, and preferably in a solution comprising a 1:50 to 1:400 dilution of said eutectic solvent in water or an aqueous buffer.

Pharmaceutical compositions and formulations of the eutectic solvents and/or photosensitizers of the present invention for topical administration may include transdermal patches, ointments, lotions, creams, gels, drops, suppositories, sprays, liquids, mouthwash, and powders. Conventional pharmaceutical carriers, aqueous, powder, dressings, or oily bases, thickeners and the like may be necessary or desirable.

Compositions and formulations of the eutectic solvents and/or photosensitizers of embodiments of the present invention for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations of the eutectic solvents and/or photosensitizers of embodiments of the present invention for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present disclosure include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations, which may conveniently be presented in unit dosage form, may be prepared according to conventional techniques well known in the pharmaceutical industry.

The compositions may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions, such as dyes, flavoring agents, preservatives, antioxidants, opacifiers, thickening agents and stabilizers. However, such materials, when added, should not unduly interfere with the biological activities of the components of the compositions. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the active agents of the formulation.

In some embodiments, eutectic solvents (e.g., comprising photosensitizers) are administered in combination with an additional therapeutic agent (e.g., antibiotic, antifungal, or chemotherapeutic agent).

Classes of antibiotics include, but are not limited to, macrolides (e.g., erythromycin), penicillins (e.g., nafcillin), cephalosporins (e.g., cefazolin), carbapenems (e.g., imipenem), monobactam (e.g., aztreonam), other beta-lactam antibiotics, beta-lactam inhibitors (e.g., sulbactam), oxalines (e.g. linezolid), aminoglycosides (e.g., gentamicin), chloramphenicol, sufonamides (e.g., sulfamethoxazole), glycopeptides (e.g., vancomycin), quinolones (e.g., ciprofloxacin), tetracyclines (e.g., minocycline), fusidic acid, trimethoprim, metronidazole, clindamycin, mupirocin, rifamycins (e.g., rifampin), streptogramins (e.g., quinupristin and dalfopristin) lipoprotein (e.g., daptomycin), polyenes (e.g., amphotericin B), azoles (e.g., fluconazole), and echinocandins (e.g., caspofungin acetate).

Examples of specific antibiotics include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

Examples of chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES).

In some embodiments, pharmaceutical compositions are administering in a maintenance or ongoing manner (e.g., one or more times a day, two or more times a day, one or more times a week, etc.). In some embodiments, compositions are administered continuously (e.g., via a skin patch, bandage, or time release formulation). In some embodiments, compositions are administered once, twice, 5 times, 10 times or more. In some embodiments, compositions are administered over a period of weeks, months, years or indefinitely.

II. Uses

In some embodiments, eutectic solvents described herein (e.g., optionally comprising a photosensitizer) find use in the killing of bacteria or fungi and in tumor targeting.

In some embodiments, eutectic solvents find use in the killing of bacteria or fungi in medical and industrial applications. In some embodiments, bacteria or fungi are in wounds or other body parts and eutectic solvents are administered to a surface of the body. In some embodiments, bacterial or fungal infections are internal and eutectic solvents are administered orally or paternal.

In some embodiments, bacteria or fungi on surface are killed (e.g., to decontaminate medical devices, food, or food preparation surfaces).

In some embodiments, eutectic solvents (e.g., comprising a photosensitizer) are used to target tumors. For example, in some embodiments, a tumor targeting agent (e.g., antibody) is used to deliver a composition comprising a eutectic solvent and a photosensitizer (e.g. optionally further comprising a chemotherapeutic agent).

In some embodiments, following administration of a eutectic solvent comprising a photosensitizer to a body part, tumor, or surface, the composition is treated with a light source to active the photosensitizer. The present disclosure is not limited to a particular source of light or energy. Any source of energy at the appropriate wavelength to activate the photosensitizer is specifically contemplated.

EXAMPLES

Example 1

Materials and Methods
NADES Preparation

The two components of each deep eutectic solvent investigated (Table 1) were dissolved in warm water (~50° C.) and evaporated at 45° C. for 15 min with a rotatory evaporator. The liquid obtained was transferred to plastic tubes with a tight cap. Water content was determined by Karl Fischer titration (C20 Coulometric KF Titrator, Mettler Toledo Inc., Schwerenbach, Switzerland).

TABLE 1

Constituents of the natural deep eutectic solvents investigated.

| Component 1 | Component 2 | Molar ratio | Acronym |
|---|---|---|---|
| Citric acid | Sucrose | 1:1 | CS |
| Citric acid | D-(+)-trehalose | 2:1 | |
| Citric acid | Choline chloride | 1:1 | |
| Citric acid | Choline chloride | 1:2 | |
| Choline chloride | DL-malic acid | 1:1 | |
| Choline chloride | DL-malic acid | 1:3 | |
| Choline chloride | Maleic acid | 1:1 | MC |
| Choline chloride | Maleic acid | 1:3 | |
| Choline chloride | Glycerol | 1:1 | GC |
| D-(+)-glucose | Sucrose | 1:1 | |
| D-(+)-glucose | D-(-)-fructose | 1:1 | |
| D-(+)-glucose | DL-malic acid | 1:1 | MG |
| Sucrose | D-(-)-fructose | 1:1 | |
| Sucrose | DL-malic acid | 1:1 | |
| Sucrose | Maleic acid | 1:1 | |

Solubility Test

Solubility test was performed by saturating the NADES in polypropylene tubes with an excess amount of THPP (chemical structure shown in FIG. 1; meso-tetra(p-hydroxyphenyl)porphine, Frontier Scientific Inc., UT, USA). The dry powder was given 1 h to sink into the viscous liquid before the tubes were agitated horizontally on an Edmund Bühler shaker (at 250 rpm) protected from light at ~22° C. for 16 h. The tubes were centrifuged (6918 g, 60 min, 22° C.) before visual evaluation of solubility potential (i.e. colouration, particle distribution and dissolution). Four NADES were selected for further studies (CS, MC, GC and MG, cf. Table 1). After centrifugation triplicate samples of the solutions were filtered (0.45 µm, Spartan) and diluted 100 times with methanol to be analysed by HPLC at detection wavelengths 419 nm and 445 nm. The HPLC analysis was performed with isocratic elution on an Ultra Biphenyl 3 µm column (100×2.1 mm; Restek Corporation, Bellefonte, Pa., USA). The mobile phase was composed of 0.34% (w/v) sodium acetate and 0.48% (w/v) sodium chloride (pH 5.2 adjusted with acetic acid using a pH 526 MultiCal® pH meter, WTW GmbH, Weilheim, Germany) and methanol (15:85). The retention time of THPP at flow 0.35 ml/min was equal in methanol and in NADES diluted more than 50 times in methanol: approximately 4.3 min at a column temperature of 30° C. The selected NADES had to be diluted more than 50 times prior to HPLC analysis due to the high viscosity.

Photostability of THPP

Investigation of the photostability of THPP in selected NADES and in methanol was performed by irradiation in a Suntest CPS+ equipped with a 1.8 kW xenon lamp and a glass filter (cut off ~310 nm) according to Option 1 (ICH Guideline Q1B).21 The samples were exposed at 765 W/m$^2$ (310-800 nm) to an endpoint corresponding to 1.2×10$^6$ lux·h (400-800 nm). The photostability of THPP was investigated in methanol and in undiluted CS and MG (cf. Table 1) containing 1×10$^{-3}$ M THPP, in NADES containing THPP diluted 50 times (to 1×10$^{-5}$ M THPP) in methanol and in MilliQ water, and of 1×10$^{-5}$ M THPP in pure methanol. Three parallels of each sample for irradiation and as dark controls were prepared in small glass containers (light path ~3 mm) covered with cling film. The dark controls were additionally covered with aluminium foil. The maximum temperature at the surface of the containers was measured with temperature recording strips (37-65° C., VWR International, LLC, West Chester, Pa., USA). Small samples (100 µl) for quantification by HPLC were withdrawn from each container before irradiation, hourly during the first 3 hours, then after 5 h and approximately 8 h (corresponding to 1.2×10$^6$ lux·h). The undiluted samples containing 1×10$^{-3}$ M THPP were diluted 100 times with methanol and the samples containing 1×10$^{-5}$ M THPP were diluted 10 times before quantification with the previously described HPLC method (2.2 Solubility test).

Polarity Measurements

Polarity ($E_{NR}$) testing of NADES was performed with Nile red (NR) as a solvatochromatic probe. A small amount of NR was added to each deep eutectic solvent. The recorded absorption maximum ($\lambda$max) of NR was applied in the formula $E_{NR}$ (kcal·mol$^{-1}$)=hc$\lambda$maxNA=28591/$\lambda$max where h is Planck's constant, c is the velocity of light and NA is Avogadro's number (Ogihara W, et al., *Chem Lett* 2004; 33: 1414-1415; Saxena R, et al., *Chem Phys Lipids* 2014; 183: 1-8).

Absorption Spectroscopy

Absorption spectra were recorded between 190 and 700 nm on a Schimadzu UV-2101 PC UV-Vis scanning spectrophotometer using a quarts cuvette with 1 cm cell path. Deep eutectic solvents containing 0.1 mg/ml THPP were diluted 0-200 times in MilliQ water. Solutions of THPP were also prepared in methanol, in MilliQ water (by dilution of a stock solution of THPP in methanol to a residual of 1% (v/v) methanol), formic acid (diluted with 50% (v/v) MilliQ water) and 5% (v/v) concentrated ammonia solution in MilliQ water. All samples were made in triplicate.

Stability of THPP in Diluted NADES

Selected NADES containing 0.1 mg/ml THPP were diluted in MilliQ water 10-200 times (n=2). Absorption and fluorescence maxima and intensity were measured after 0-6 weeks after dilution. Fluorescence spectroscopy was performed on a Photon Technology International modular fluorescence system (London, Ontario, Canada) with Model 101 monochromator with f/4 0.2-m Czerny-Turner configuration. The instrument was equipped with a red-sensitive photomultiplier. An excitation and emission correction was automatically performed. The excitation and emission monochromator band passes were set at 2 nm and excitation wavelength at the absorption maximum of the solutions. Correction for absorbance at excitation maximum was performed manually with all samples. All measurements were performed in a quarts cuvette with 1 cm cell path at ~22° C. As precipitation of sugar was observed in 100-200 times diluted CS solutions after 4 weeks and in all CS solutions after 6 weeks, these samples were filtered (0.45 µm, Spartan 13/0.45 RC filter, Schleider & Schull, Dassel, Germany) before measurements.

Bacterial Phototoxicity of THPP

*Enterococcus faecalis* (ATCC 19433) and *Escherichia coli* (ATCC 25922) were resuspended from glycerol at −20° C. in tryptone soy broth (TSB; Oxoid Ltd., Basingstoke, UK) and incubated (37° C.) for 24 h. Aliquots from the overnight cultures were diluted to $OD_{600}$ 0.03 in phosphate buffered saline without Ca$^{2+}$ and Mg$^{2+}$ (PBS, Lonza, Verviers, Belgium) and transferred to culture plate wells (24-well; Flat Bottom Cell+, Sarstedt, Inc., Newton, N.C., USA) for studies of the bacteria in the stationary phase. For studies in the exponential phase aliquots from the overnight cultures were resuspended in TSB and incubated (37° C.) to $OD_{600}$ 0.6. The bacterial suspensions were then centrifuged (4000 g, 22° C., 10 min), TSB was replaced with PBS and dilution to $OD_{600}$ 0.03 was performed. CS and MG were prepared with 50-500 nM THPP to give a final concentration of photosensitiser of 0.5-5 nM after dilution 100 times in PBS. Reference supersaturated solutions of THPP were prepared by diluting a stock solution of THPP in ethanol with PBS; the final amount of ethanol was 1% (v/v). Bacterial suspensions in PBS were mixed (1:1) with PBS (controls), CS or MG with and without THPP diluted in PBS or with reference THPP solution. Each assay contained one culture plate for irradiation and one for dark controls. *E. faecalis* samples were incubated (37° C.) for 10 min before irradiation, irradiated for 10 min (corresponding to 11 J/cm$^2$±10%) and incubated (37° C.) again for 10 min. Irradiation was performed in a previously described light-polymerisation unit containing three blue light fluorescent tubes emitting mainly blue light in the wavelength range 400-500 nm (FIG. 2). 24 After irradiation the samples were diluted 40 times in PBS prior to incubation. *E. coli* samples were incubated (37° C.) for 30 min prior to irradiation, irradiated for 30 min (corresponding to 32 J/cm$^2$±10%) and subsequently incubated (37° C.) for 60 min. The samples were diluted 60 times in PBS after irradiation. After the final incubation the samples were plated onto TSB agar using an automatic spiral plater (Whitley, Don Whitley Scientific Ltd., Shirley, England, UK). Bacterial survival was estimated after 24 h incubation (37° C.) by counting CFUs using a colony counter (Acolyte, Symbiosis Europe, Cambridge, UK). Each treatment was performed with 8 parallels.

Results
Characterization of Selected NADES

The prepared NADES had a water content of ~20% (w/w) and were more polar than methanol (51.9 kcal/mol) and water (48.2 kcal/mol; Table 2). Addition of excess THPP in the NADES (Table 1) indicated the best solubilizing properties of the NADES named CS, MG, MC and GC (cf. Table 1). The selected four NADES appeared green. They were chosen to be further analyzed by HPLC. The other solutions of THPP were either clear with blue particles or pale bluish green with THPP particles. The amount of solubilized THPP in the selected NADES is listed in Table 2. MG was the best solvent of the chosen eutectics and GC the poorest. Storage of the solutions for three days induced a change of colour of THPP in GC from green to brown. CS and MG proposed the best solubilising properties and were therefore studied further.

TABLE 2

Solubility of THPP, water content and polarity of selected deep eutectic solvents (n = 3).

| NADES | THPP (mg/ml) | Water content (% (w/w)) | $E_{NR}$ (kcal/mol)[1] |
|---|---|---|---|
| CS | 0.093 ± 0.003 | 22.0 ± 1.5 | 44.1 |
| MG | 1.036 ± 0.041 | 22.1 ± 3.2 | 47.7 |
| MC | 0.007 ± 0.004 | 18.3 ± 2.8 | 44.6 |
| GC | n.d. | n.i. | 47.9 |

[1]$E_{NR}$ = hcNA/λmax = 28591/λmax.
n.d. = below the detection limit (2.17 × 10$^{-8}$ M) of the HPLC method.
n.i. = not investigated.

Absorption Spectroscopy

Figure 3:
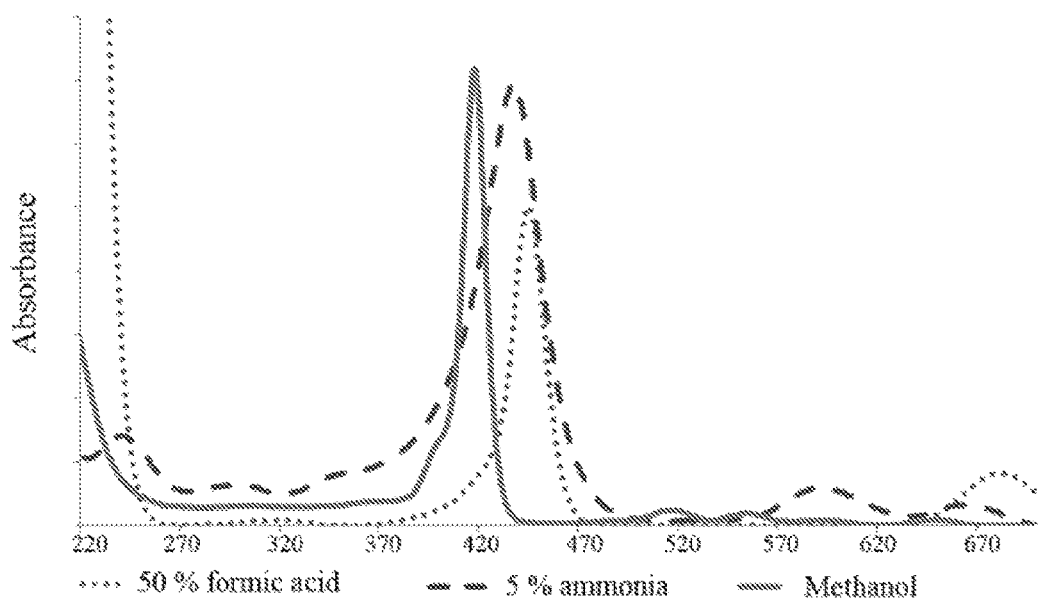
FIG. 3 shows absorption spectra of THPP in 50% formic acid, 5% ammonia and in methanol.
Figure 4:
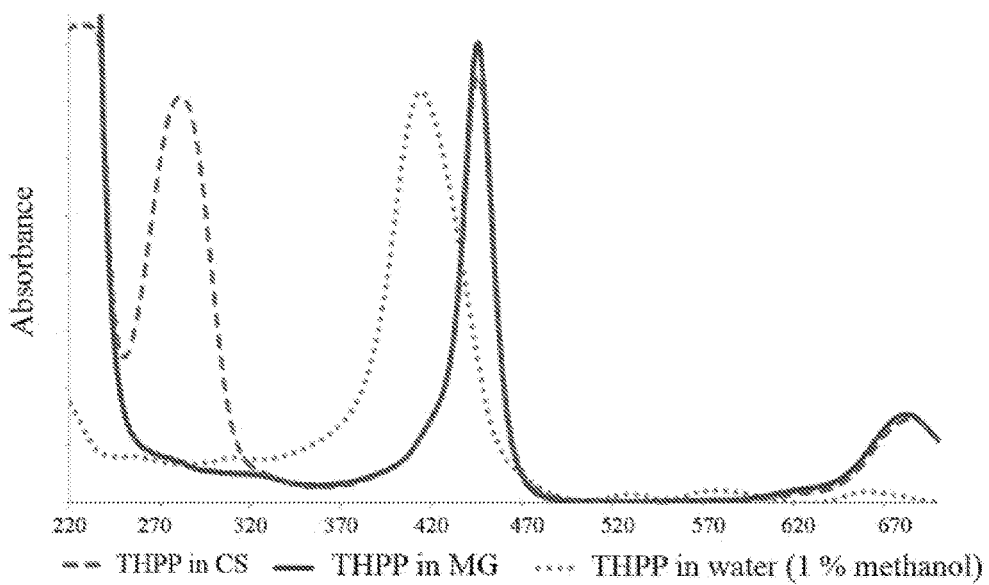
FIG. 4 shows absorption spectra of THPP in CS and MG (both diluted 50 times in water) and in water prepared by dilution (100 times) of a stock solution in methanol.

The absorption spectrum of THPP in methanol (dark red solution) showed a maximum at 419 nm (Soret band) and four Q-bands at 517 nm, 555 nm, 593 nm and 650 nm respectively (FIG. 3). After a 100-fold dilution of a solution of THPP in methanol with purified water the solution turned yellow and the Soret band was slightly blue shifted (414 nm) and the Q-bands changed to 529 nm, 578 nm and 661 nm respectively (FIG. 4). In formic acid the Soret band of THPP was red shifted to 445 nm, the four Q-bands disappeared and a new band appeared at 682 nm (FIG. 3). The absorption maximum of THPP in ammonia was at 438 nm and two Q-bands appeared at 594 nm and 664 nm respectively (FIG. 3).

Absorption spectra of CS and MG could not be obtained without dilution due to inner filter effect. The eutectic solvents without THPP (diluted ≥10 times in water) showed minimal absorbance above 350 nm. Upon addition of THPP to MG and CS followed by dilution 10-50 times in water, the Soret band of THPP was red shifted to 445 nm and only one Q-band at 682 nm was visible (FIG. 4). Further dilution (100-200 times in water) did not result in any further shift in the absorption spectra, and the absorbance was linear with respect to the dilution factor.

Stability of THPP in Diluted NADES

Figure 5A:
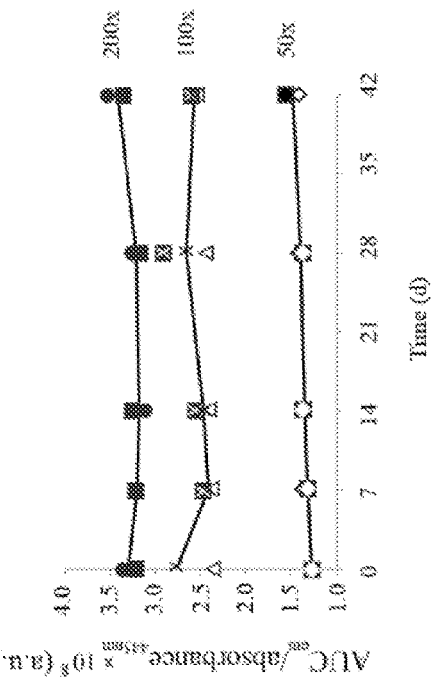
FIG. 5A-C shows area under the curve ($AUC_{em}$) of the emission band (650-800 nm) divided by the absorbance (a.u.) at the excitation wavelength after 0-42 d storage at ~22° C. protected from light (average of n=2±the highest and lowest $AUC_{em}$/absorbance$_{445\ nm}$ value).
Figure 5B:
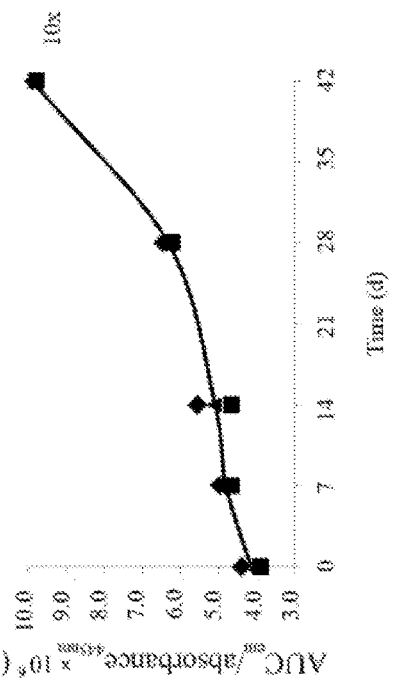
Figure 5C:
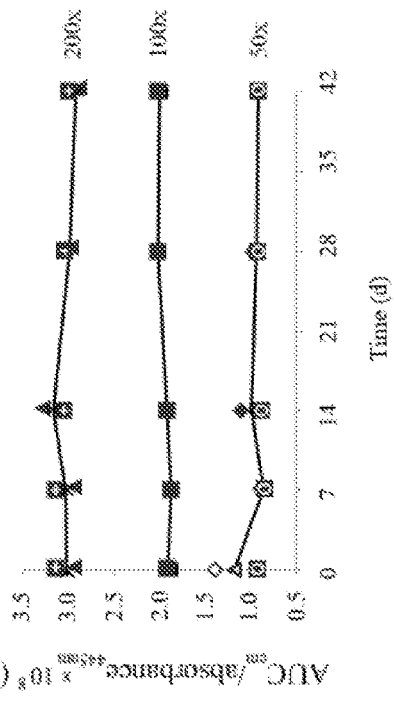

Samples of THPP in CS and MG diluted 10-200 times in water and stored for up to 6 weeks showed non-linear changes in fluorescence intensity, area under the emission curve ($AUC_{em}$, 650-800 nm) and emission maximum. The absorbance wavelength maximum remained constant (445 nm) as the samples were diluted 10-200 times and during storage. The reduction in absorbance at 445 nm upon dilution was linear. The absorbance decreased in a linear manner in all samples during 6 weeks of storage (2-30%). An increase in fluorescence intensity that was inversely proportional to the decrease in absorbance was also observed for these samples during storage. Samples diluted 50 and 100 times resulted in the highest and most stable fluorescence intensity. The samples diluted 100 and 200 times, however, were the most stable with respect to the ratio $AUC_{em}$/absorbance$_{445\ nm}$ (Table 3). The Stoke's shift varied within 5% during storage of all samples (Table 3). A plot of $AUC_{em}$/absorbance$_{445\ nm}$ was made to observe the concentration independent change in fluorescence (FIG. 5). The 10-fold dilution of CS showed a linear increase (r=0.951) in $AUC_{em}$/absorbance$_{445\ nm}$ with time, whereas the 50-fold dilution showed a non-linear increase in $AUC_{em}$/absorbance$_{445\ nm}$, and the 50-fold dilution of MG an overall decreasing trend in $AUC_{em}$/absorbance$_{445\ nm}$ (FIG. 5). The other dilutions showed only minor changes in $AUC_{em}$/absorbance$_{445\ nm}$ during storage (Table 3). Quantification of THPP in the diluted samples, performed by HPLC at $t_0$ (freshly made dilutions of samples of THPP in CS and MG that had been stored for 42 d) and after 42 d ($t_{42}$), revealed a 5-80% reduction in THPP concentration in the diluted samples after storage (results not shown). The highest reduction was seen in 200 times diluted CS (80% vs. 30% in MG) and the lowest reduction in MG diluted 50 and 100 times (10% and 5%, respectively). The THPP concentration decreased more in diluted CS than in diluted MG during storage. No new peaks were observed in the HPLC chromatograms after storage for 42 d. Precipitation of sugars was observed in 100-200 times diluted CS solutions after 28 d and in all CS solutions after 42 d and may have entrapped some THPP. Otherwise no precipitation of THPP was observed.

A supersaturated solution of THPP prepared from a stock solution in methanol by dilution with MilliQ water (1% residual methanol) was not physically stable, as demonstrated by a 25% decrease in absorbance at 418 nm after 3 h. In comparison, the absorbance of the 50 and 100 times diluted MG and CS with THPP decreased 1-3% after 7 days and totally 2-15% after 6 weeks (results not shown). The largest decrease was observed in the NADES diluted 200 times.

TABLE 3

Emission (em) maxima of each diluted NADES containing THPP (n = 2) after 0 ($t_0$) and 42 d ($t_{42}$) storage, the Stoke's shifts and % change in $AUC_{em}$/absorbance$_{445\ nm}$. The Stoke's shifts are based on the Q-band at 682 nm. $\lambda_{ex}$ $t_0$-$t_{42}$ was 445 mm.

| Preparation | Dilution factor | $\lambda_{em}$ (nm) $t_0$ | $\lambda_{em}$ (nm) $t_{42}$ | Stoke's shift (nm) $t_0$ | Stoke's shift (nm) $t_{42}$ | $\Delta t_0 \to t_{42}$ $AUC_{em}$/$abs_{445\ nm}$ (%) |
|---|---|---|---|---|---|---|
| CS | 10  | 735 ± 4 | 738 ± 1 | 53 ± 4 | 56 ± 1 | +139 |
| CS | 50  | 732 ± 2 | 733 ± 1 | 50 ± 2 | 51 ± 1 | +16 |
| CS | 100 | 731 ± 1 | 731 ± 1 | 49 ± 1 | 49 ± 1 | −7 |
| CS | 200 | 728 ± 0 | 730 ± 0 | 46 ± 0 | 48 ± 0 | +4 |
| MG | 50  | 735 ± 1 | 732 ± 1 | 53 ± 1 | 50 ± 1 | −23 |
| MG | 100 | 731 ± 0 | 732 ± 2 | 49 ± 0 | 50 ± 1 | +5 |
| MG | 200 | 732 ± 1 | 733 ± 3 | 50 ± 1 | 51 ± 3 | −3 |

Photostability of THPP

Figure 6A:
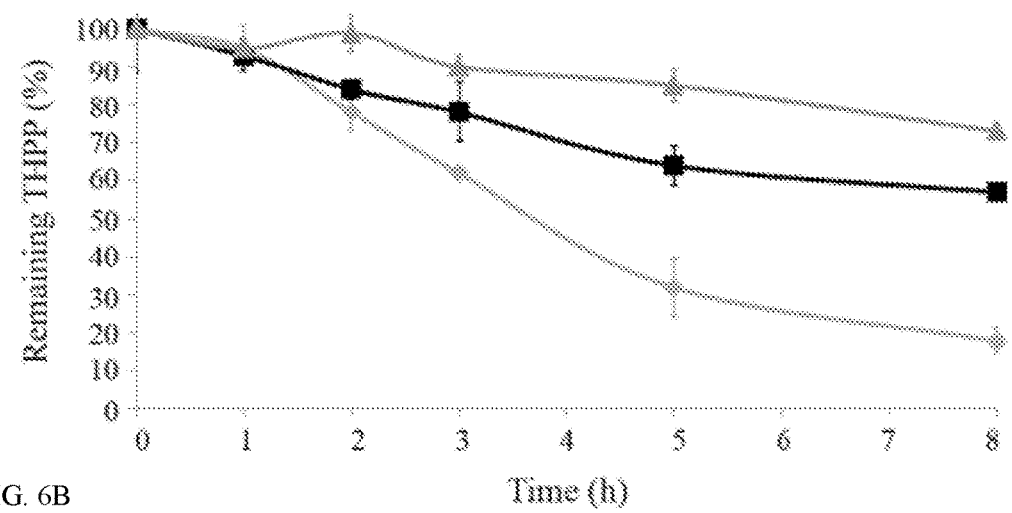
FIG. 6A-B shows a) Photostability of $1\times10^{-3}$ M THPP in methanol (diamond), in undiluted CS (square) and in undiluted MG (triangle). b) Photostability of $1\times10^{-5}$ M THPP in methanol (diamond), in MG diluted 50 times in water (triangle) or in methanol (x), and in CS diluted 50 times in water (square) or in methanol (circles).
Figure 6B:
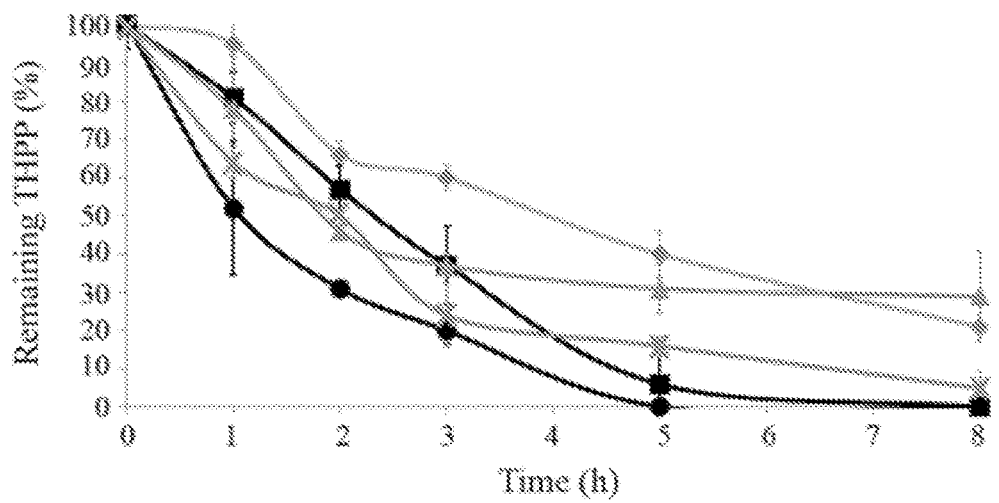

THPP in undiluted NADES was more photostable than in methanol at equal concentration (FIG. 6a). THPP appeared slightly more photostable in the NADES diluted in water compared to NADES diluted in methanol (FIG. 6b). The degradation was more rapid in the diluted NADES samples than in pure methanol containing the same amount of THPP.

Bacterial Phototoxicity

Figure 7A:
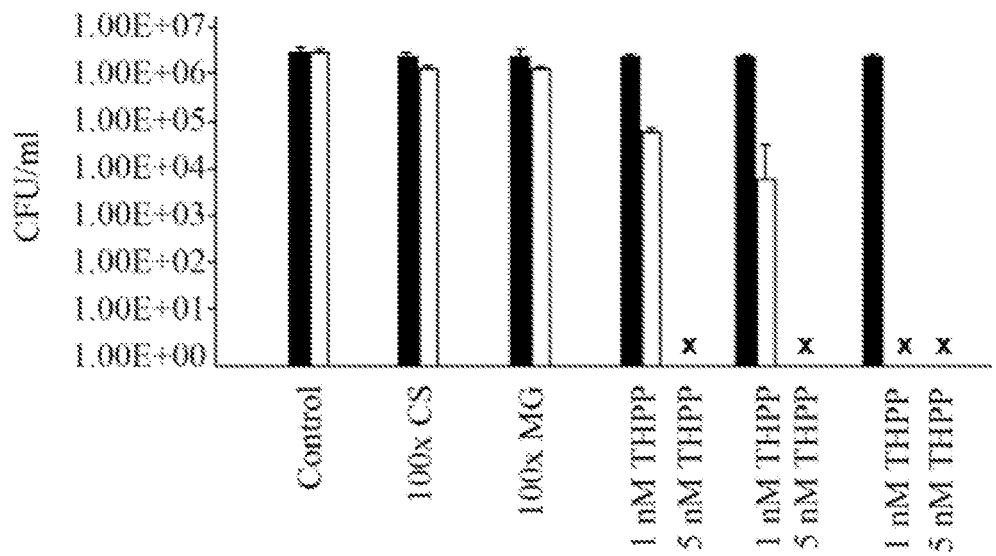
FIG. 7A-B shows viable bacteria after treatment in the stationary phase expressed as mean colony forming units per ml (CFU/ml)+SD. The bacteria were exposed to THPP either in PBS (containing 1% ethanol) or in CS or MG diluted 100 times in PBS. Black columns=non-irradiated samples; white columns=irradiated samples; x=no viable bacteria. a) *E. faecalis*; light dose 11 J/cm². b) *E. coli*; light dose 32 J/cm².
Figure 7B:
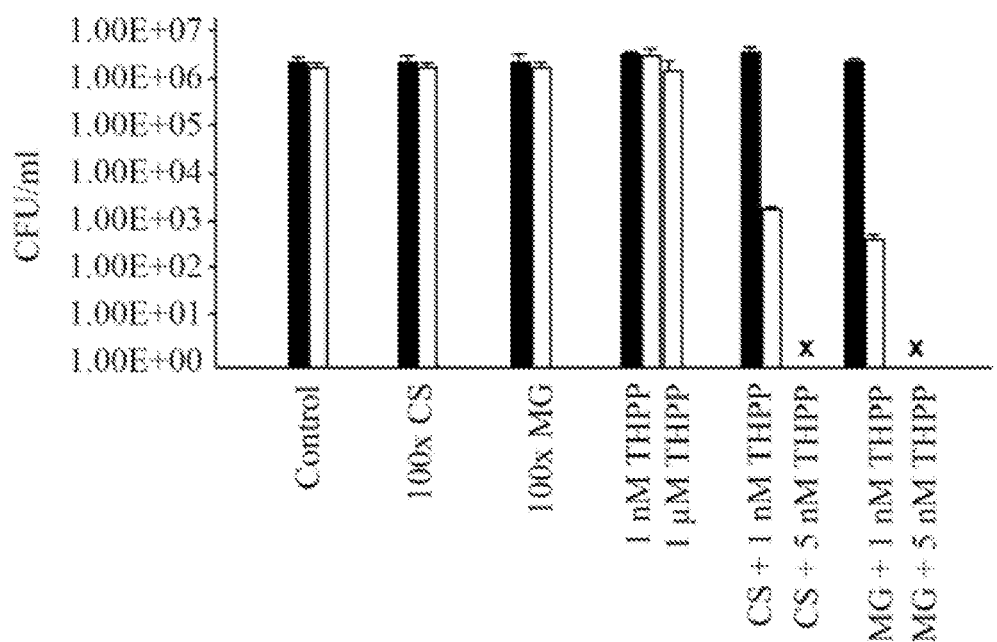

CS and MG diluted 100 times with PBS induced approximately 0.4 log reductions in viable E. faecalis and E. coli upon irradiation (FIG. 7). A supersaturated solution of THPP in PBS (made from a stock solution in ethanol to a final amount of 1% (v/v) ethanol) combined with blue light resulted in complete photoinactivation of E. faecalis in the stationary phase at 5 nM concentration (FIG. 7a). On E. coli in the stationary phase 1 µM and 10 µM supersaturated THPP solution induced a log 0.4 and 2.3 log reduction in viable bacteria, respectively. Samples of 5 nM THPP prepared in CS and MG (concentration after a 100-fold dilution with PBS) resulted in no viable E. faecalis and E. coli in the stationary phase (FIG. 7). E. faecalis was also completely photoinactivated by 1 nM THPP in the diluted MG preparation (FIG. 7a). In the exponential phase, only 0.5 nM and 1 nM THPP in CS and MG (concentration after dilution 100 times with PBS) were needed for complete photoinactivation of E. faecalis and E. coli, respectively.

Conclusions

The neutral p-hydroxyphenyl porphyrin THPP was selected as PS to challenge the solubilizing properties of the NADES and the current understanding of the lack of bacterial phototoxicity of neutral porphyrins. The selected four NADES contained ~20% (w/w) water and were more polar than water, yet solubilised THPP well. For comparison, THPP in pure water adhered to the walls of the container above the liquid surface and showed no interaction with the solvent. The proposed structure of NADES resembling liquid crystals where the molecules are arranged through hydrogen bonding and other intermolecular interactions (Dai Y, et al., Anal Chim Acta 2013; 766: 61-68). The water remaining after preparation also participate in the macromolecular structure (Dai Y, et al., supra). The solubilizing effect of the NADES on THPP was probably due to intermolecular hydrogen bonding and proton donor-acceptor interactions. Different spacing and number of hydrogen donors and acceptors of the NADES are possibly some of the reasons why some NADES solubilised THPP well while others were poor solubilisers of this porphyrin.

A PS should exhibit both hydrophilic and hydrophobic properties to be able to interact with and penetrate the bacterial outer structure. 3 THPP is a relatively hydrophobic porphyrin with a log P value of 4.0. (Ormond A B, et al., Dyes Pigm 2013; 96: 440-448). The hydrophobicity and lack of cationic charge could lower the interaction probability between the PS and the bacteria and result in formation of cytotoxic species at a non-lethal distance from the bacteria upon irradiation. In that respect we designed very hydrophilic formulations of THPP without encapsulating THPP in a carrier that would prolong its release time from the vehicle. Once mixed with a bacterial suspension, THPP remained dissolved in a hydrophilic solution in close contact with the target bacteria, allowing improved interactions and generation of reactive oxygen species (ROS) close to the target. The amount of THPP in NADES needed to induce >6 log reductions in viable E. coli (5 nM THPP) was remarkably lower than in the reference solution of THPP (at best 2.3 log reductions with 10 µM THPP in PBS). The 0.4 log reduction of viable E. coli exposed to 1 µM THPP in PBS indicates that low concentrations of THPP in PBS are negligible phototoxic to E. coli. Increasing the concentration of THPP to 10 µM and 20 µM both resulted in 2.3 log reductions in viable bacteria, implying that increasing the concentration of THPP only results in aggregation, filter effect and little additional phototoxic effect. The THPP concentration needed for complete photoinactivation of both bacteria in the presence of NADES was also lower than the amount required of similar neutral porphyrins described in the literature (Banfi S, et al., J Photochem Photobiol B: Biol 2006; 85: 28-38; Konan Y N, et al., Eur J Pharm Sci 2003; 18: 241-249; Nitzan Y, et al., Photochem Photobiol 1995; 62: 342-347). Even though THPP is a neutral porphyrin, which several times have been reported to be less phototoxic than cationic porphyrins, the PS proved to be very phototoxic once in the right formulation. THPP was more phototoxic to E. faecalis and E. coli in the exponential phase than in the stationary phase. This may be explained by the activation of the RpoS system in the stationary phase and in situations with increased environmental ROS (Imlay, Nat Rev Microbiol 2013; 11: 443-454).

Figure 8:
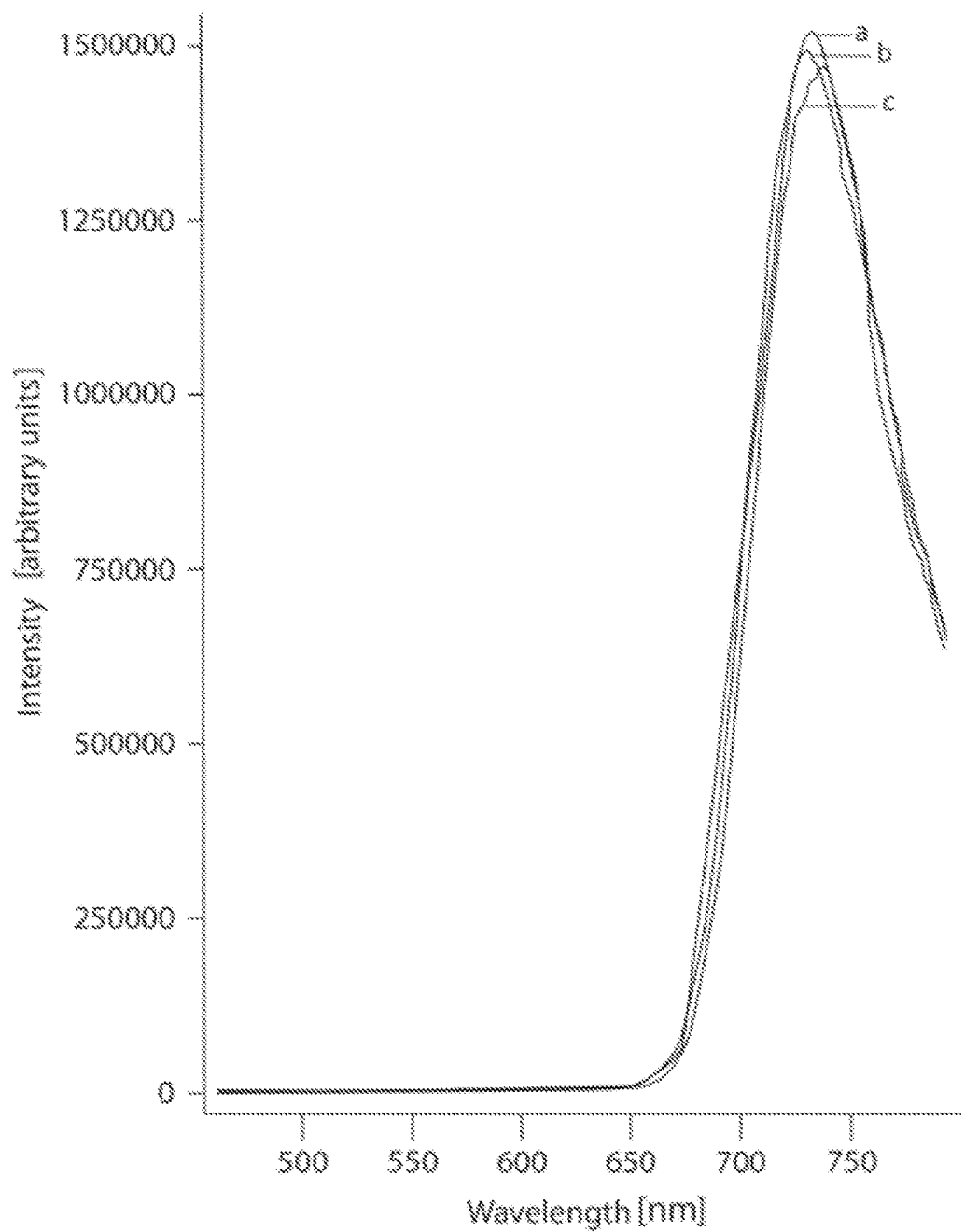
FIG. 8 shows normalized fluorescence spectra of 3 µM THPP in a) MG diluted 50 times in MilliQ water, b) CS diluted 50 times in MilliQ water and c) in 10% (v/v) formic acid.

The absorption spectra of THPP in CS and MG were comparable to the spectrum of THPP in 50% (v/v) formic acid (FIGS. 3 and 4). These spectra are similar to those of THPP dissolved at pH below 4 (Sobczyński J, et al., Pharmazie 2013; 68: 100-109; Guo Xm. J Mol Struct 2008; 892: 378-383). Sobczyński et al. (2013) asserted that the Q-band was characteristic for the protonated porphyrin core (Sobczyński J, et al., Pharmazie 2013; 68: 100-109). The similarity between the absorption spectra of THPP in NADES and in formic acid indicates the formation of the protonated form of THPP in NADES. It is not unlikely that the acids in selected NADES (e.g. citric acid in CS and malic acid in MG) can donate a hydrogen atom to a pyrrole in THPP, thus yielding a cationic porphyrin with one or several positive charges. The assertion that NADES may act like a protic solvent and thus solubilise several poorly water-soluble compounds has been suggested (Dai Y, et al., supra; Paiva A, et al., ACS Sustainable Chem Eng 2014; 2: 1063-1071). The similarities between the fluorescence spectra of THPP in NADES and in 10% (v/v) formic acid confirms the presence of the protonated form of THPP in selected NADES (FIG. 8). Guo et al. explained the bathochromic shift of the Soret band and the one Q-band of THPP as J-aggregate shapes due to formation of two-valence porphyrin cations (Guo Xm. J Mol Struct 2008; 892: 378-383). In line with this suggestion the absorption spectra obtained for THPP in NADES indicate that J-aggregates are formed. The fluorescence pattern, however, does not show evidence of the formation of J-aggregates in NADES. THPP has two emission bands at approximately 658 nm and 722 nm in ethanol, chloroform, DMF and in aqueous solutions of cyclodextrins (Ormond A B, Freeman H S. *Dyes Pigm* 2013; 96: 440-448; Guo Xm. *J Mol Struct* 2008; 892: 378-383; Puglisi A, et al., *New J Chem* 2007; 31: 1499-1506). J-aggregates are characterised inter alia by a small Stoke's shift. THPP in NADES has only one emission band at approximately 732 nm (FIG. 8), which is a fairly large Stoke's shift (50 nm based on the Q-band). The emission peak is symmetrical and indicates only one emitting specie.

The solubilising effect of 5% ammonia on THPP was hypothesised to be due to ionisation of the porphyrin, similar to that observed in formic acid. However, the two Q-bands were not consistent with the Q-bands of THPP in methanol, acids (FIG. 3) and NADES (FIG. 4). The changes in absorbance of THPP in strong base were therefore assumed to be due to deprotonation of the phenols (Guo X, et al., *J Photochem Photobiol A: Chem* 2005; 173: 258-263). The ionisation and change in molecule symmetry resulted in a bathochromic shift, a wide Soret band and two Q-bands due to the presence of different deprotonation states of THPP. The presence of coexisting absorbing species (i.e. monomers and aggregates) can also be the reason for the wide Soret band (~70 nm) of THPP in water (containing 1% (v/v) methanol; FIG. 4). Dilution of the solution of THPP in pure methanol a 100-fold with water resulted in a slight blue shift which can be attributed to H-aggregates and distortion of the porphyrin ring (Puglisi A, et al., *New J Chem* 2007; 31: 1499-1506; Eisfeld A, Briggs *J. Chem Phys* 2006; 324: 376-384).

The increase in $AUC_{em}$/absorbance$_{445\ nm}$ during storage of CS diluted 10 and 50 times indicates the formation of a more structured system. The THPP molecules seem to be rigidified in the NADES network resulting in a higher fluorescence quantum yield (without any changes in the absorption spectrum; FIG. 5). As the absorption spectra remained unchanged during storage, except for the reduction of absorbance as THPP precipitated, there was no apparent change in monomer or aggregate state. The previously mentioned decrease in THPP concentration in MG and CS diluted 200 times (approximately 30% and 80%, respectively) during 6 weeks of storage did not coincide with the minimal change in $AUC_{em}$/absorbance$_{445\ nm}$ of the same preparations (Table 3). This finding supports the theory that THPP is solubilised in the NADES network which becomes more rigid during storage. The dramatic increase in $AUC_{em}$/absorbance$_{445\ nm}$ during storage of the 10-fold dilution of CS indicates that this rigidification is more pronounced in these samples (FIG. 5a). Further dilution loosens the network which results in more molecular mobility and hence reduced fluorescence. The reduction in $AUC_{em}$/absorbance$_{445\ nm}$ during storage of 50-fold diluted MG showed that the structure of the NADES affects the reaction pattern of THPP, i.e. which deactivation pathway is prioritised. The most pronounced decrease in absorbance at 445 nm after storage of the 200-fold dilutions compared to the other dilutions was probably owing to the formation of the cationic form of THPP due to the acid content in the NADES and the less structured network. Upon dilution of the NADES in water the equilibrium between the neutral and cationic THPP was shifted toward the neutral form which has very low aqueous solubility. Formation of J-aggregates of THPP dissolved in this solvent is unlikely based on these results. The important observation from this stability study is that the solubilising interactions between NADES and THPP still remain intact even upon extensive dilution and storage for several weeks.

Several factors may contribute to the photostabilisation of THPP in NADES such as higher viscosity leading to a slower reaction rate and formation of stabilising intermolecular H-bonds between the NADES and THPP. The slower photodegradation in undiluted NADES than in pure methanol was probably due to the presence of a stabilising NADES network. In methanol THPP appeared more available for photochemical degradation due to lack of a protective surrounding network. THPP forms aggregates in methanol at this concentration ($1 \times 10^{-3}$ M). The photostabilising effect of the NADES was apparently higher than the shielding effect obtained by aggregate formation in methanol. The finding that the porphyrin was more photostable in NADES diluted in water than in methanol may be explained by the following. Addition of large amounts of methanol (e.g., a 50-fold dilution) to the NADES might break the NADES network with the result that THPP was solubilised primarily by methanol. Dilution of the NADES 50 times in water appeared to maintain the solubilising NADES network, and kept THPP in a cationic form (probably mostly in the monomeric state due to electrostatic repulsion). High viscosity may contribute to the stabilising properties of undiluted, but not diluted NADES. The photostability of THPP in NADES diluted more than 50 times was lower than in pure methanol in spite of a slightly higher viscosity in the former solution. Intermolecular interactions between THPP and the NADES and the unique NADES network appear to be the most prominent photostabilising factors in undiluted NADES. Many of these interactions are disturbed upon dilution.

Solubilization of THPP in a hydrophilic medium without encapsulation in nanoparticles gives immediate contact between the drug and the target bacteria. THPP was dissolved in NADES and the formulation could easily be diluted in aqueous medium without immediate precipitation of THPP. Even though neutral porphyrins like THPP have been regarded as less phototoxic towards Gram-negative bacteria, only nanomolar amounts of THPP in NADES were needed for complete photoinactivation of *E. coli*. The physical- and photochemical stability of THPP in NADES in undiluted samples were superior to diluted samples indicating that these preparations should be stored undiluted. Once diluted, samples can be stored for several weeks at room temperature protected from light. NADES as a delivery principle of poorly water soluble drugs shows a great potential in aPDT.

Example 2

Preparation of Selected NADES

The two components of each deep eutectic solvent investigated in this study (Table 4) were dissolved in warm water (~50° C.) and evaporated at 45° C. for 15 min with a rotary evaporator. The desired amount of THPP (meso-tetra(p-hydroxyphenyl)porphine, Frontier Scientific Inc., UT, USA) or curcumin (synthesised according to the method of Pabon[20]) for phototoxicity studies on bacteria was then added. The dry powder was given 1 h to sink into the viscous liquid followed by agitation on an Edmund Bühler shaker (at 250 rpm) protected from light at ~22° C. until the dyes were completely dissolved

TABLE 4

Constituents of the natural deep eutectic solvents investigated.

| Component 1 | Component 2 | Molar ratio | Acronym |
|---|---|---|---|
| Citric acid | Sucrose | 1:1 | CS |
| Choline chloride | Maleic acid | 1:3 | CM |
| D-(+)-glucose | Sucrose | 1:1 | GS |
| D-(+)-glucose | DL-malic acid | 1:1 | MG |

Antibacterial Phototoxicity

Figure 2:
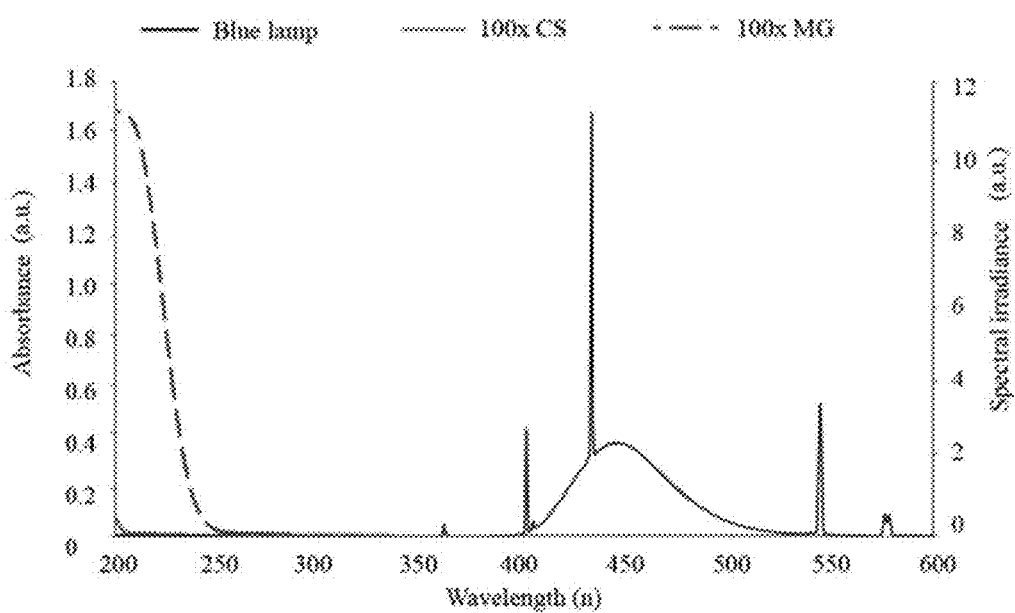
FIG. 2 shows absorption spectra of CS and MG (diluted 100 times in water, left axis) and the emission spectrum of the irradiation chamber equipped with three blue fluorescent tubes (right axis).

Escherichia coli (ATCC 25922) and Enterococcus faecalis (ATCC 19433) were resuspended from glycerol at −20° C. in tryptone soy broth (TSB; Oxoid Ltd., Basingstoke, UK) and incubated (37°) for 24 h. The bacterial suspensions were then centrifuged (4000 g, 22° C., 10 min) and TSB was replaced with phosphate buffered saline without $Ca^{2+}$ and $Mg^{2+}$ (PBS, Lonza, Verviers, Belgium). The suspensions were further diluted with PBS to $OD_{600}$ 0.03. Equal amounts of diluted bacterial suspension and NADES dilutions were mixed in culture plate wells (24-well, Flat Bottom Cell+, Sarstedt, Inc., Newton, N.C., USA). The NADES containing curcumin or THPP were diluted 13-100 times with PBS prior to the bacterial study. Each assay contained one culture plate for irradiation and one for non-irradiated samples. E. faecalis samples were incubated (37° C.) for 10 min before irradiation, irradiated for 10 min (corresponding to 11 $J/cm^2 \pm 10\%$) and incubated (37° C.) again for 10 min. After treatment the samples were diluted 40 times in PBS prior to plating onto agar plates. E. coli samples were incubated (37° C.) for 30 min prior to irradiation, irradiated for 30 min (corresponding to 32 $J/cm^2 \pm 10\%$) and subsequently incubated (37° C.) for 60 min. The samples were diluted 60 times in PBS before plating onto TSB agar. Irradiation was performed in a previously described irradiation chamber (Polylux PT, Deve, Unna, Germany) emitting mainly blue light in the wavelength range 400-500 nm. The emission spectrum of the radiation source equipped with three blue light fluorescent tubes is shown in FIG. 2. The culture plates for dark treatment were incubated (37° C.) in darkness for 30 min (E. faecalis) or 2 h (E. coli). After treatment the samples were plated onto TSB agar using an automatic spiral plater (Whitley, Don Whitley Scientific Ltd., Shirley, England, UK). Bacterial survival was estimated after 24 h incubation (37° C.) by counting colony forming units (CFU) using a colony counter (Acolyte, Symbiosis Europe, Cambridge, UK). Each treatment was performed with 8 parallels. The reduction in viable bacteria after each treatment was compared to untreated control samples.

Figure 9:
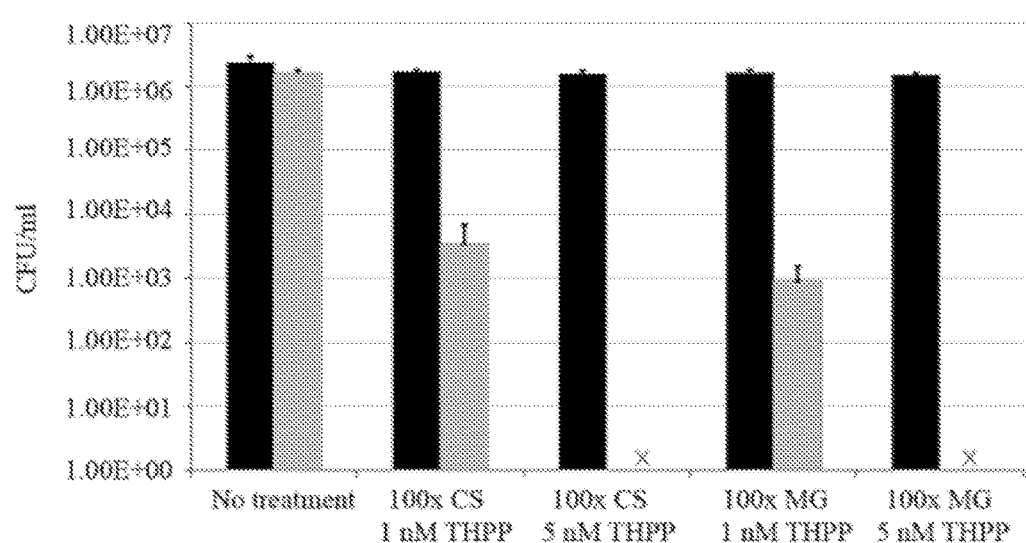
FIG. 9 shows viable *E. coli* expressed as mean colony forming units per ml (CFU/ml) +SD. The bacteria were exposed to THPP dissolved in CS and MG diluted a 100-fold in PBS. The final concentration of THPP was 1 nM or 5 nM THPP. Black columns=non-irradiated samples; green columns=irradiated samples (blue light dose 32 J/cm²); x=no viable bacteria.
Figure 10:
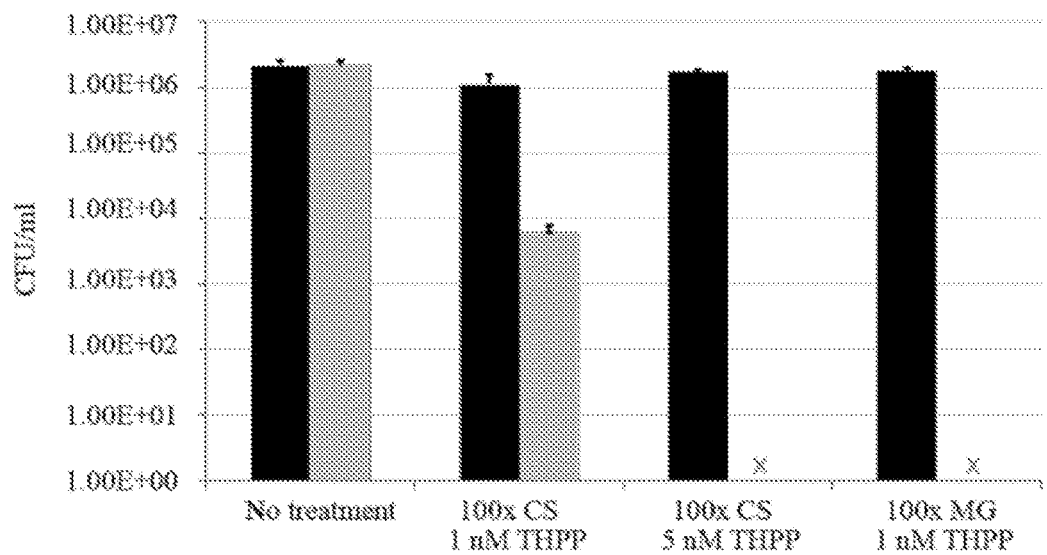
FIG. 10 shows viable *E. faecalis* expressed as mean colony forming units per ml (CFU/ml)+SD. The bacteria were exposed to THPP dissolved in CS and MG diluted a 100-fold in PBS. The final concentration of THPP was 1 nM or 5 nM THPP. Black columns=non-irradiated samples; green columns=irradiated samples (blue light dose 11 J/cm²); x=no viable bacteria.
Figure 11:
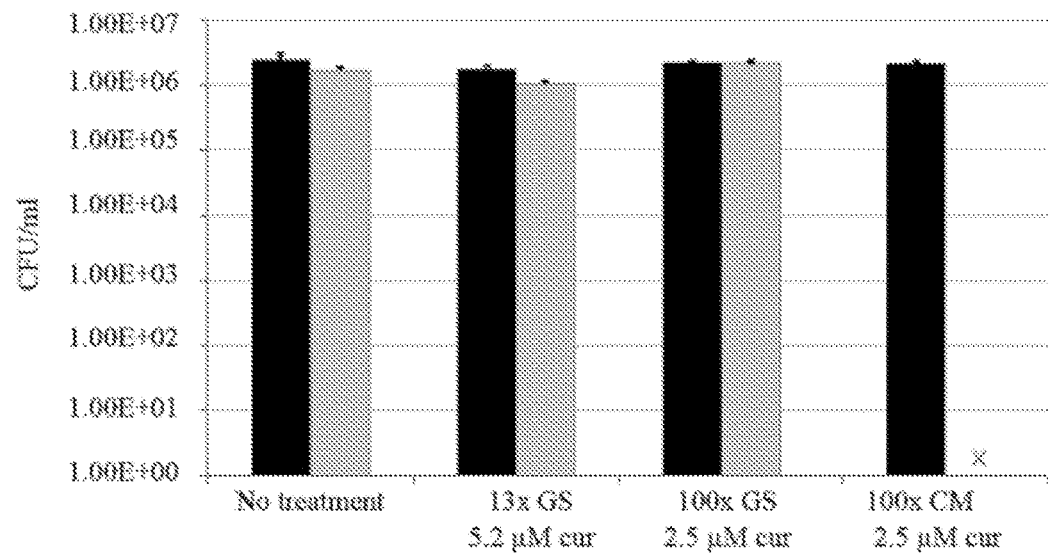
FIG. 11 shows viable *E. coli* expressed as mean colony forming units per ml (CFU/ml)+SD. The bacteria were exposed to curcumin dissolved in GS (diluted 13- and 100-fold in PBS) and CM (diluted a 100-fold in PBS) to 5.2 µM and 2.5 µM curcumin. Black columns=non-irradiated samples; orange columns=irradiated samples (blue light dose 32 J/cm²); x=no viable bacteria.

E. coli was completely photoinactivated by THPP dissolved in CS and MG diluted 100 times to a final concentration of 5 nM THPP (FIG. 9). The THPP concentration could be further reduced to 1 nM in diluted MG and still induce complete photoinactivation of E. faecalis (FIG. 10). A 100-fold dilution of CM to a final curcumin concentration of 2.5 µM resulted in complete photoinactivation of E. coli (FIG. 11). However, the same curcumin concentration in GS was not phototoxic to the same bacterium (FIG. 11). Dilution of CS, MG and CM less than a 100-fold resulted in NADES-induced phototoxicity (results not shown).

Conclusion

Preparation of curcumin and THPP in selected NADES for aPDT increased the phototoxic potential of the PS drastically. NADES find use for delivering established and new PS, including substances which previously have been regarded as unsuitable in PDT due to their low water solubility, lack of cationic charge and tendency to aggregate in aqueous media (e.g., THPP).

Example 3

NADES without photosensitizer were prepared as described in Example 2. Bacterial phototoxicity studies on E. coli were performed as described in Example 2.

The results from the study of selected NADES on E. coli are displayed in Table 5. CM, even after dilution 50 times with PBS, was highly toxic to the bacteria in the absence of light and resulted in a complete eradication of E. coli (Table 5). CS and MG diluted 50 times with PBS were moderately dark toxic to the bacteria, but were highly phototoxic (Table 5). Further dilution of CS and MG 100 times with PBS reduced the overall toxicity towards E. coli, but still resulted in a significant reduction of viable bacteria ($p<0.01$).

TABLE 5

Percent reduction of viable E. coli after treatment with selected NADES with and without irradiation with mainly blue light (32 J/cm2). n.s. = no significant reduction. A 100 % reduction corresponds to no detected CFUs after treatment.

| | Dilution 1:50 (% reduction) | | Dilution 1:100 (% reduction) | |
|---|---|---|---|---|
| NADES | Dark toxicity | Phototoxicity | Dark toxicity | Phototoxicity |
| CS | 60.7 | 100 | 43.9 | 56.0 |
| CM | 100 | 100 | n.s. | n.s. |
| GS | n.s. | n.s. | n.s. | n.s. |
| MG | 77.4 | 100 | 48.9 | 72.9 |

Conclusion

The NADES CM, CS and MG showed a high antibacterial potential. The study demonstrated that the antibacterial effect of CS and MG was potentiated even by very low light doses at wavelengths where these NADES have a minor absorption. CM was highly toxic both in the absence and presence of light.

Example 4

Antibacterial Activity of Natural Deep Eutectic Solvents (NADES)

Natural deep eutectic solvents (NADES) are postulated to be a vital part of all living cells and bacteria as a solvent where non-water soluble compounds interact with water-soluble enzymes in a medium where they are all soluble. NADES resembles honey in a way that honey also is a eutectic solvent composed of glucose and fructose in addition to several other components. Honey, being a natural product, is difficult or impossible to standardise, while NADES can be prepared and characterised in the laboratory. As honey has been used as a natural antibacterial treatment for many years, the antibacterial properties of NADES were investigated. These properties cannot be ascribed to the individual compounds that make up the NADES but rather the unique NADES network originating from defined ratios of these compounds present in NADES.

Materials and Methods

Preparation of the Samples

The NADES presented in Table 6 were prepared as described in Example 1. Briefly, the components were mixed and dissolved in warm water (~50° C.) before evaporation of the solvent at 45° C. for 15 min with a rotatory evaporator. The resulting NADES were transferred to polypropylene tubes with a tight cap. The individual components of each NADES were also prepared as solutions in MilliQ water in a concentration similar to the concentration in the final NADES preparation. All samples were diluted 1:1 with bacterial suspension ($OD_{600}$ 0.03) or 1:50, 1:100 and 1:200 with phosphate buffered saline (PBS, pH 7.4, Lonza, Verviers, Belgium) prior to dilution 1:1 with the bacterial suspension immediately before the bacterial studies.

TABLE 6

The constituents of each natural deep eutectic solvent investigated.

| NADES no. | Molar ratio | Component 1 | Component 2 | Component 3 |
|---|---|---|---|---|
| 3 | 1:1 | Citric acid | Sucrose | — |
| 14 | 2:1 | Choline chloride | Citric acid | — |
| 21 | 2:1 | Choline chloride | Maleic acid | — |
| 26 | 5:2 | Choline chloride | Xylitol | — |
| 35 | 1:1 | Citric acid | Xylitol | — |
| 40 | 1:1:1 | DL-malic acid | D-(−)-fructose | D-(+)-glucose |

Bacterial Studies

*Enterococcus faecalis* (ATCC 19433), *Staphylococcus aureus* (strain Newman) and *Escherichia coli* (ATCC 25922) were re-suspended from glycerol at −20° C. in tryptone soy broth (TSB; Oxoid Ltd., Basingstoke, UK) each day and incubated at 37° C. for 24 h. The overnight cultures were centrifuged (4000 g, 22° C., 10 min), the medium replaced and diluted with PBS to $OD_{600}$ 0.03. The bacterial suspensions were mixed 1:1 with the samples described in the previous paragraph. A volume of 200 µl from each sample was transferred to the first and seventh well on each row on a 96 well plate (Nunclon sterile 96 well plate with lid, Thermo Fischer Scientific, Waltham, Mass.). Two identical plates were made each time, one for light treatment and one for dark controls. The plates containing *E. faecalis* or *S. aureus* samples were incubated for 10 min (37° C.), irradiated with blue light for 10 min (corresponding to 9.5 $J/cm^2$±10%) and incubated again for 10 min (37° C.). The plates containing *E. coli* samples were incubated for 30 min (37° C.), irradiated with blue light for 30 min (corresponding to 27 $J/cm^2$±10%) and incubated again for 30 min (37° C.). The plates containing the dark controls were treated similarly, but covered with aluminium foil during the irradiation period and placed beside the irradiation chamber. Irradiation was performed using a previously described light polymerisation unit equipped with three fluorescent tubes emitting mainly blue light in the 400-500 nm range (intensity maximum wavelength 450 nm, see Example 1). After treatment, the samples were diluted according to the 6×6 drop plate procedure, modified to 4×4 (each treatment was performed with four parallels). A volume of 15 µl from each dilution was then plated onto TSB agar plates, left to dry for a few minutes and incubated overnight (37° C.). Viable colony forming units (CFU)/ml were calculated by counting the CFUs, multiplying with the dilution factor and dividing by the application volume.

Determination of statistically significant differences in viable bacteria after photodynamic treatment was performed using a two-sample t-test (Minitab 17, Minitab Inc., Coventry, UK). A p-value of less than 0.05 was considered statistically significant.

Results and Discussion

Citric acid (2.7 M before dilution with PBS) was toxic to *E. faecalis* at dilution ratios 1:1 up to 1:100. This was expected as several bacteria only can survive a short period of time at very low pH. After dilution 1:200, the pH in the citric acid solution increased to ~3 which did not reduce the number of viable colony forming units during the total period of treatment (30 min). At dilution 1:200, even though the citric acid solution no longer was toxic to *E. faecalis*, NADES 3 resulted in 98% reduction in viable bacteria after light treatment. After dilution more than 1:100 with PBS, NADES 3 showed no dark toxicity towards *E. faecalis*.

As observed with NADES 3 and its components, NADES 14 and NADES 35 also resulted in complete photoinactivation of *E. faecalis* at dilution 1:1 and 1:100 with PBS due to the citric acid component. At dilution 1:200 none of the components of NADES 14 and NADES 35 alone were toxic to *E. faecalis*, yet NADES 14 resulted in 99.9% photoinactivation of the bacterium and 81% reduction in viable colony forming units after 30 min incubation in the dark. NADES 35 diluted 1:200 with PBS resulted in complete photoinactivation of *E. faecalis* and 97.8% reduction in viable bacteria after 30 min dark treatment. Even after dilution 1:400 NADES 35 was significantly phototoxic to *E. faecalis*, resulting in 97.8% photoinactivation after light treatment (p<0.05). Dark toxicity was not observed. These NADES thus possessed an antibacterial effect which was not due to either of the individual components, but rather the unique NADES.

Maleic acid (3.1 M) was very toxic to *E. faecalis* and resulted in complete eradication of the bacterium even after dilution 1:400 with PBS. Even though choline chloride was not toxic to *E. faecalis*, NADES 21 also resulted in complete eradication of the bacterium at dilutions 1:1 to 1:400 with PBS, probably due to the content of maleic acid. Malic acid (2.1 M before dilution with PBS) was also quite toxic to *E. faecalis*, resulting in complete photoinactivation of the bacterium at dilutions 1:1 and 1:100 with PBS (FIG. 1F). Similarly, NADES 40 at equal dilutions also induced complete photoinactivation of *E. faecalis*. However, at dilution 1:200 with PBS NADES 40 were 18 times more phototoxic than the malic acid solution, resulting in 99.99% photoinactivation of *E. faecalis* (FIG. 1F). The other components of NADES 40, fructose and glucose, were not toxic to the bacterium. The phototoxic effect of this NADES was evident.

The pH-neutral NADES 26 and its separate components did not possess any major antibacterial effects towards *E. faecalis* and *S. aureus* under the given experimental conditions even though a reduction of 28-32% viable colony forming units per ml was statistically significant.

*S. aureus* was more tolerant to citric acid than the other investigated bacteria. The 1:1 dilution of the 2.7 M citric acid solution did result in complete eradication of the bacterium, but after dilution 1:100 the citric acid solution was not toxic anymore. The NADES investigated in this study containing citric acid, i.e. NADES 3, NADES 14 and NADES 35, resulted in no surviving colony forming units after dilution 1:1 with bacterial suspension due to the citric acid component. After dilution 1:100, however, NADES 3 resulted in 75% photoinactivation, NADES 14 resulted in 60% photoinactivation (FIG. 2B) and NADES 35 resulted in 81% photoinactivation of *S. aureus*. As none of the individual components of the NADES were toxic to *S. aureus* at this dilution, the phototoxicity was due to the unique NADES. NADES 35 could even be diluted 1:200 with PBS and still induce a significant 70% photoinactivation of *S. aureus*.

Maleic acid (3.1 M before dilution with PBS) was quite toxic to *S. aureus*. Dilution ratios 1:1 up to 1:200 resulted in complete eradication of the bacterium after a total treatment period of 30 min, both with the maleic acid solutions and the dilutions of NADES 21. After dilution 1:400 the maleic acid solution was no longer toxic to *S. aureus*, but neither was NADES 21.

Malic acid (2.1 M before dilution) was toxic to *S. aureus* at dilution 1:1, but not toxic after dilution 1:100. Not surprisingly, NADES 40 also resulted in complete eradication of *S. aureus* at dilution 1:1, but also resulted in 65% photoinactivation of viable bacteria after dilution 1:100 when none of its individual components were toxic. This NADES clearly possessed higher antibacterial effect than its individual components.

Citric acid prepared as a 1:1 dilution from a 2.7 M stock solution, similar to the concentration present in the NADES containing this acid, was very toxic to *E. coli*. This was probably due to the very low pH which neither Gram-negative nor Gram-positive bacteria can endure for long. Therefore, NADES 3 also resulted in complete eradication of *E. coli* at dilution 1:1, both with and without irradiation with blue light. The same observations were made for NADES 3 and its components diluted 1:100 with PBS. The pH of the citric acid solution and NADES 3 now increased to approximately pH 2.5, which the bacterium could endure for the period of the study (1.5 h). However, both citric acid and NADES 3 were phototoxic at this dilution, and killed all the bacteria present upon irradiation with blue light. At dilution 1:200 only NADES 3 was phototoxic, with 97.8% reduction in viable *E. coli* (FIG. 3A). The components of NADES 3 were not toxic at this dilution. Therefore, the antibacterial effect seen was due to the unique NADES.

A similar observation was made with NADES 14 and NADES 35 on *E. coli*. As these NADES also contained citric acid, a dilution up to 1:100 resulted in complete eradication of the bacteria after photodynamic treatment with the NADES or with the citric acid solution. Again, the NADES at this dilution was more phototoxic than dark toxic to *E. coli*. At dilution 1:200, NADES 14 and NADES 35 resulted in complete photoinactivation of *E. coli*, and even 99.8% (NADES 14) and 99.9% (NADES 35) reduction in viable bacteria after dark treatment. Neither of the components was toxic at this dilution. NADES 35 could even be diluted 1:400 with PBS and still result in 99.95% photoinactivation of *E. coli* in combination with blue light and 92% inactivation after incubation in the dark for 1.5 h.

The NADES are eutectic solvents formed at specific molar ratios between its solid state components and water. The NADES network probably breaks at extensive dilution with another solvent. Therefore, the toxicity of NADES 21 could not be separated from the toxicity of maleic acid as 3.1 M maleic acid was highly toxic to *E. coli* even at dilution 1:400. Malic acid (2.1 M) was also highly toxic to *E. coli*, resulting in a reduction in viable bacteria after treatment with the 1:1 dilution and 1:100 dilution of this acid. No additional antibacterial effect was observed for NADES 40 on *E. coli* compared to the pure malic acid solution.

The pH-neutral NADES 26 composed of the non-toxic components choline chloride (concentration 5 M) and xylitol (concentration 2.3 M) was highly phototoxic to *E. coli* at dilution 1:1 with the bacterial suspension. NADES 26 diluted 1:1 resulted in no viable bacteria in combination with 27 J/cm² blue light, while it resulted in 99.7% reduction in viability without irradiation. After dilution more than 1:1, minor antibacterial effect was observed (although a significant reduction of 23% viability after dark or light treatment was observed after dilution 1:100 (p<0.05)).

Conclusion

The different NADES possessed different antibacterial effects on *E. faecalis*, *S. aureus* and *E. coli* depending on their composition and dilution with PBS prior to the treatments. The NADES containing acids appeared most toxic to the bacteria; after minor dilution probably mostly due to the low pH, but sometimes also at higher dilutions were the individual components no longer were toxic to the bacteria. The pH-neutral NADES 26 was highly phototoxic to the Gram-negative bacterium *E. coli* at dilution 1:1. In cases where the NADES were more toxic to the bacteria than their individual components, it was evident that the eutectic which comprised the NADES possessed other properties than the individual components making up the eutectic solvent. Some of the NADES possessed antibacterial effect without irradiation with blue light. In several cases, this antibacterial effect could be enhanced upon Example 5

Potentiation of the Antibacterial Phototoxicity of a Cationic Porphyrin in Natural Deep Eutectic Solvents (NADES)

It is a general belief that photosensitisers with a positive charge (e.g., cationic photosensitisers) are more phototoxic for bacteria in antimicrobial photodynamic therapy (aPDT) than negatively charged or neutral photosensitisers. In this study, the cationic photosensitiser tetra-(4-trimethylanilinum)-porphine tetrachloride (TMAP,

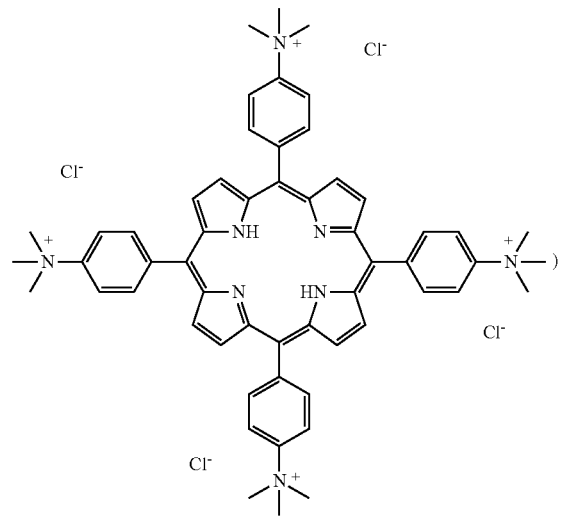

was chosen as a model compound (porphyrin). The photosensitiser was dissolved in four different NADES and compared to corresponding solutions in phosphate buffered saline (PBS, pH 7.4) and in a citric acid solution (pH ~4). NADES 14 and NADES 35 contain citric acid which makes them highly acidic prior to dilution, while NADES 26 and NADES 39 only contain neutral compounds which results in a neutral pH (Table 7).

TABLE 7

The components of the NADES investigated in this study and the dilution of the final preparations in phosphate buffered saline and bacterial suspension in the phototoxicity studies.

| NADES no. | Molar ratio | Component 1 | Component 2 | Final dilution |
|---|---|---|---|---|
| 14 | 2:1 | Choline chloride | Citric acid | 1:400 |
| 26 | 5:2 | Choline chloride | Xylitol | 1:200 |

TABLE 7-continued

The components of the NADES investigated in this study and the dilution of the final preparations in phosphate buffered saline and bacterial suspension in the phototoxicity studies.

| NADES no. | Molar ratio | Component 1 | Component 2 | Final dilution |
|---|---|---|---|---|
| 35 | 1:1 | Citric acid | Xylitol | 1:800 |
| 39 | 5:2 | Choline chloride | D-(−)-fructose | 1:100 |

Materials and Methods

Preparation of the Samples

The NADES were prepared as previously described (see Example 1). Briefly, the components of each NADES (see Table 7) were mixed and dissolved in a round flask with 50 ml of warm water (~50° C.) before evaporation of the solvent at 45° C. for 15 min with a rotatory evaporator. TMAP (Frontier Scientific, Inc., Logan, Utah, USA) was then added to each NADES. The samples were diluted from 1:100 up to 1:800 with PBS to exclude the toxicity of the NADES itself (see Example 4). In a clinical setting, the antibacterial effect of the NADES itself would be a positive supplement to the phototoxic effect of the photosensitiser. The final concentration of TMAP was 1 nM. Samples of TMAP were also prepared in purified water (MilliQ) to be 1 nM after dilution 1:200 with PBS (pH 7.4, Lonza, Verviers, Belgium) or with a 6.8 mM citric acid solution (pH ~4) and bacterial suspension. The citric acid solution (2.7 M) was diluted totally 1:400 with PBS and bacterial suspension to have the same pH and citric acid concentration as the similarly diluted NADES 14 and NADES 35.

Bacterial Studies

The bacterial studies were performed on *Enterococcus faecalis* (ATCC 19433), *Staphylococcus aureus* (strain Newman) and *Escherichia coli* (ATCC 25922) as described in Example 4.

Results and Discussion

TMAP is a cationic porphyrin which is assumed to be highly phototoxic to Gram-positive and Gram-negative bacteria due to electrostatic interactions with the negatively charged bacterial membrane. Indeed, even at 1 nM concentration TMAP induced a reduction in viable bacteria following light treatment. Only the outer nitrogens of TMAP are protonated in pH-neutral solutions. It is assumed that also the inner nitrogens become protonated in acidic solutions below pH ~4.5. It was therefore postulated that TMAP dissolved in PBS and pH-neutral NADES would be quite phototoxic to the bacteria, while TMAP dissolved in acidic solutions and in acidic NADES would be even more phototoxic.

TMAP was not exceedingly phototoxic when dissolved in pure PBS. The phototoxicity towards *E. faecalis*, *S. aureus* and *E. coli* increased upon dissolution in the citric acid solution. The phototoxicity of 1 nM TMAP towards the Gram-positive bacteria increased upon dissolution in NADES 14 (acidic), NADES 26 (neutral) and NADES 39 (neutral) and towards *E. coli* upon dissolution in NADES 14 (acidic) and NADES 35 (acidic). The NADES containing TMAP were diluted in PBS according to Example 4 resulting in no additional phototoxicity from the NADES themselves. Even though the pH value of NADES 14 and NADES 35 after dilution with PBS was the same as, or slightly higher than the citric acid solution, 1 nM TMAP in NADES induced an extensive increase in phototoxicity. The phototoxicity of TMAP in NADES 14 towards *E. faecalis* increased 35 times when compared to the citric acid solution. In the slightly less acidic NADES 35 (due to the dilution with PBS), however, TMAP appeared less phototoxic than in the citric acid solution. This was probably due to less protonation of TMAP in this highly diluted NADES. Even though the pH was neutral in NADES 26 and NADES 39, 1 nM TMAP was even more phototoxic to *E. faecalis* in these preparations than in the citric acid solution, and TMAP in NADES 39 was even more phototoxic than TMAP in the acidic NADES 14. There were other factors than the pH and charge of TMAP which influenced the phototoxicity of the porphyrin on this bacterium.

TMAP (1 nM) was more or less equally phototoxic to *S. aureus* in the citric acid solution and in NADES 14. TMAP in the pH-neutral NADES 26 and NADES 39 were the most phototoxic towards *S. aureus*. The preparation of TMAP in PBS (pH-neutral) was much less phototoxic. Again, the NADES effect was apparent and proved equally or more important for the synergistic antibacterial effect than the simple pH effect of the acidic NADES. Increasing the concentration of TMAP from 1 nM increased the bacterial phototoxicity of all preparations.

One or more cationic charge on the porphyrin has been deemed necessary for any phototoxicity towards Gram-negative bacteria like *E. coli*. The native cationic charges of TMAP were not enough to make this porphyrin significantly phototoxic at 1 nM concentration in PBS or the neutral NADES 26 and NADES 39 (p>0.05). TMAP (1 nM) resulted in only 0.2% surviving colony forming units in the citric acid solution and in the diluted NADES 14. This corresponds to 10 000 surviving colony forming units per ml. However, 1 nM TMAP in NADES 35 (even after dilution 1:800 with PBS) resulted in no viable *E. coli* after photodynamic treatment. These results on *E. faecalis*, *S. aureus* and *E. coli* demonstrate the unique properties of NADS to enhance the phototoxic potential of a cationic porphyrin. Photochemical eradication of Gram-positive and Gram-negative bacteria by TMAP has not previously been reported at the 1 nM level.

The phototoxic potential of the cationic porphyrin TMAP was potentiated by selected NADES. TMAP (1 nM) showed the highest phototoxic potential on *E. faecalis* when dissolved in the neutral NADES 39. TMAP was equally phototoxic towards *S. aureus* when prepared in the neutral NADES 26 and NADES 39. TMAP in the acidic NADES 35 showed the highest phototoxicity on *E. coli*. The results indicate that the Gram-positive bacteria were more sensitive to the less charged TMAP while the Gram-negative bacterium was more sensitive to the more positively charged photosensitiser. In all cases it was observed that the phototoxic potential of TMAP was more potentiated by NADES than by equally acidic PBS or citric acid solutions. Bringing together the results from this study and the studies on pure NADES in Example 4, it is evident that the antibacterial effect of NADES can be enhanced upon addition of a photosensitiser like TMAP combined with blue light.

Example 6

Antibacterial Phototoxicity of an Anionic Porphyrin in Natural Deep Eutectic Solvents (NADES)

Negatively charged photosensitisers are rarely used in antimicrobial photodynamic therapy due to the expected lack of phototoxicity. This may be a result of electrostatic repulsion between the negatively charged photosensitiser and the overall negatively charged outer membrane of the bacteria. This example investigated the antibacterial phototoxic effect of the anionic porphyrin tetra-(4-carboxyphenyl)-porphine (TCPP,

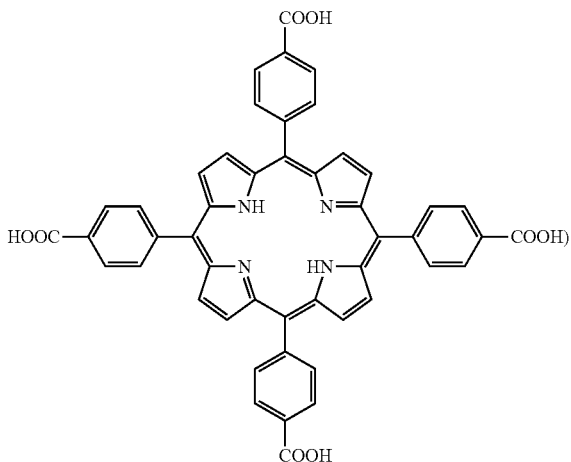

upon dissolution in NADES as opposed to a simple solution in phosphate buffered saline (PBS, pH 7.4) or a citric acid solution (pH ~4).

Materials and Methods

Preparation of the Samples

The NADES were prepared as previously described (see Example 1). Briefly, the components of each NADES were mixed and dissolved in a round flask with 50 ml of warm water (~50° C.) before evaporation of the solvent at 45° C. for 15 min with a rotatory evaporator.

TCPP (Frontier Scientific, Inc., Logan, Utah, USA) was added to each NADES. The samples were diluted from 1:200 up to 1:800 with PBS and bacterial suspension to exclude the toxicity from the NADES itself (see Example 4). The final TCPP concentrations were 0.5 nM-1 µM. Samples of TCPP were also prepared in ethanol to be 1 nM-1 µM after dilution 1:200 with PBS (pH 7.4, Lonza, Verviers, Belgium) or with a 6.8 mM citric acid solution (pH ~4) and bacterial suspension. The citric acid solution (2.7 M) was diluted totally 1:400 to have the same pH and citric acid concentration as the similarly diluted NADES 3 and NADES 14.

TABLE 8

The components of the NADES investigated in this study.

| NADES no. | Molar ratio | Component 1 | Component 2 | Component 3 |
|---|---|---|---|---|
| 3 | 1:1 | Citric acid | Sucrose | — |
| 14 | 2:1 | Choline chloride | Citric acid | — |
| 26 | 5:2 | Choline chloride | Xylitol | — |
| 40 | 1:1:1 | DL-malic acid | D-(−)-fructose | D-(+)-glucose |

Bacterial Studies

Bacterial studies were performed as described in Example 4. The studies were performed on *Enterococcus faecalis* (ATCC 19433), *Staphylococcus aureus* (strain Newman) and *Escherichia coli* (ATCC 25922) with eight parallels of each treatment.

Results and Discussion

Little phototoxicity was expected of TCPP in neutral solvents like PBS or NADES 26 as TCPP is an anionic porphyrin. Protonation of the nitrogens in TCPP due to the low pH in the citric acid solution, NADES 3, NADES 14 and NADES 40 was expected to increase the phototoxicity of this porphyrin. It was observed that 1 nM TCPP in pure PBS was not very phototoxic to the Gram-positive bacterium *E. faecalis*. The phototoxicity increased extensively in citric acid solution and in the acidic NADES 3, NADES 14 and NADES 40 with almost complete eradication of *E. faecalis* after photodynamic treatment. In the neutral NADES 26, however, the TCPP concentration had to be increased to 1 µM to induce complete eradication of the bacteria after light treatment. The same concentration of TCPP in pure PBS resulted in approximately 300 surviving colony forming units.

Similar results were obtained with the other Gram-positive bacterium, *S. aureus*. One nM TCPP in pure PBS was quite phototoxic and killed half of the viable bacteria during treatment. In PBS and in the pH-neutral NADES 26 even a 1000-fold increase in TCPP concentration up to 1 µM did not result in complete photoinactivation of all the bacteria upon irradiation. The two preparations were equally phototoxic. A pH-neutral formulation of this anionic porphyrin was not optimal to achieve complete photoinactivation of *S. aureus*. The citric acid solution and the acidic NADES preparations of TCPP were much more phototoxic. On this bacterium, 1 nM TCPP in NADES 3 resulted in no viable bacteria detected after treatment, and was the most phototoxic preparation.

TCPP (1 nM) was not phototoxic to the Gram-negative bacterium *E. coli*. The concentration was therefore increased to 40 nM. Still, TCPP in pure PBS was not phototoxic to *E. coli*. By preparing 40 nM TCPP in citric acid solution with fairly low pH, the phototoxicity of TCPP increased. This may be due to protonation of the carboxyl groups (neutralizing them) and the nitrogens, resulting in an overall positive charge. The phototoxicity increased even more when TCPP was prepared in the equally acidic NADES 3 and NADES 14. In the neutral NADES 26 and acidic NADES 40 the concentration of TCPP had to be increased even further to be phototoxic to *E. coli*. It was increased to 0.6 µM in NADES 40, which resulted in complete photoinactivation of *E. coli* while the similar concentration in citric acid solution still showed 20 000 surviving colony forming units per ml. The difference in phototoxicity of 1 µM TCPP in PBS and in NADES 26 was not statistically significant (p>0.05). The results show that other factors than the pH and charge of the solvent contributed to the phototoxicity of TCPP in NADES (the NADES effect).

Conclusion

TCPP is an anionic porphyrin yet only 1 nM was needed to induce phototoxicity in the Gram-positive bacteria when prepared in citric acid solutions and acidic NADES. Because the negatively charged, tightly organised outer membrane of the Gram-negative bacteria would repulse the negatively charged photosensitiser, the TCPP concentration had to be increased to 40 nM to observe any comparable phototoxicity on *E. coli* (in PBS and in citric acid solution). It was observed that even though TCPP was protonated in citric acid solution, the phototoxicity towards *E. coli* increased even more when TCPP was prepared in NADES 3 or NADES 14. This increase in phototoxicity was due to the synergistic antibacterial effect between the NADES and the photosensitiser in the presence of light. The NADES themselves were not phototoxic at the selected dilutions. The differences in phototoxicity on *S. aureus* were less dramatic, yet significant between the preparations of TCPP in PBS, citric acid solution and NADES 3, ranging from the least to the most phototoxic. By increasing the TCPP concentration, the porphyrin was highly phototoxic to both the Gram-positive bacteria also when prepared in the neutral NADES 26. On all the investigated bacteria, the preparations of TCPP in NADES were equally or more phototoxic than the aqueous solutions prepared with the same pH. The NADES preparations are more suitable in a clinical setting than plain aqueous solutions at equal pH. This is due to the higher viscosity and increase in physical stability of the investigated photosensitisers in NADES, and the synergistic antibacterial effect between the NADES and the activated photosensitiser (the NADES effect).

Example 7

Further Evaluation of Porphyrins in Selected Natural Deep Eutectic Solvents (NADES)

Introduction

As described above, it was observed that the photodynamically effective concentration of neutral (Example 1 and 2), cationic (Example 5) and anionic (Example 6) photosensitisers can be reduced when prepared in natural deep eutectic solvents (NADES) for eradication of Gram-positive bacteria like *Enterococcus faecalis* and *Staphylococcus aureus* and the Gram-negative bacterium *Escherichia coli*. To evaluate the phototoxic activity of two selected porphyrins prepared in NADES even further, the Gram-positive bacterium *Staphylococcus epidermidis* and the Gram-negative bacteria *Klebsiella pneumoniae* and *Pseudomonas aeruginosa* were chosen.

Materials and Methods

The selected formulations to be tested on *S. epidermidis* were tetra-(4-trimethylanilinum)-porphine tetrachloride (TMAP) and tetra-(hydroxyphenyl)-porphine (THPP) prepared in phosphate buffered saline (PBS, pH 7.4), in a citric acid solution, TMAP in the neutral NADES 26 and THPP in the acidic NADES 3. The formulations that were to be tested on *K. pneumoniae* and *P. aeruginosa* were TMAP and THPP prepared in PBS and in a citric acid solution, TMAP in the acidic NADES 35 and THPP in the acidic NADES 3. The reason that the acidic NADES 35 was exchanged for the neutral NADES 26 in the studies on the Gram-positive bacterium was because Gram-positive bacteria previously had proven easier to photoinactivate with a less charged porphyrin (Example 5) and that *S. epidermidis* was very sensitive even to highly diluted NADES 35 (>1:800). TMAP and THPP were applied in the concentration range 1-20 nM.

Preparation of the Samples

The NADES were prepared as previously described (see Example 1). Briefly, the components of each NADES (see Table 1) were mixed and dissolved in a round flask with 50 ml of warm water (~50° C.) before evaporation of the solvent at 45° C. for 15 min with a rotatory evaporator.

TMAP and THPP (Frontier Scientific, Inc., Logan, Utah, USA) were prepared in MilliQ water and ethanol, respectively, to give a final concentration of 1-20 nM in the bacterial suspension after dilution 1:200 with PBS (Lonza, Verviers, Belgium) or with a 6.8 mM citric acid solution prepared in PBS and bacterial suspension. TMAP was also prepared in NADES 26 and NADES 35, and THPP was prepared in NADES 3 by dissolving the porphyrin in the NADES on a magnetic stirrer for 2 d. The concentrations were adjusted give a final concentration of 1-20 nM porphyrin in the bacterial suspension after dilution with PBS (see Table 9). Aqueous solutions of 2.7 M citric acid, 2.3 M xylitol, 2.5 M sucrose, 5 M choline chloride and pure NADES, respectively, were used to investigate the toxicity of the individual compounds and NADES without a photosensitiser. The concentrations of the excipients were the same as in the respective NADES after evaporation of unbound water. The solutions were diluted totally 1:200 (or more) in the bacterial studies.

TABLE 9

The molar ratio and components of each natural deep eutectic solvent investigated, and the final dilution of the preparations used in the phototoxicity studies.

| NADES no. | Molar ratio | Component 1 | Component 2 | Final dilution |
|---|---|---|---|---|
| 3 | 1:1 | Citric acid | Sucrose | 1:400 |
| 26 | 5:2 | Choline chloride | Xylitol | 1:200 |
| 35 | 1:1 | Citric acid | Xylitol | 1:800 |

Phototoxicity Studies

Phototoxicity studies were performed as described in Example 4. The studies were performed on *S. epidermidis* (ATCC 35984; grown in tryptone soy broth overnight), *K. pneumoniae* (ATCC 31844; grown in brain-heart infusion broth overnight) and *P. aeruginosa* (ATCC 9027; grown in brain-heart infusion broth overnight). The studies on the Gram-positive bacterium were performed as with the Gram-positive bacteria *Enterococcus faecalis* and *Staphylococcus aureus* as described in Example 4. The studies on the Gram-negative bacteria were performed as with the Gram-negative bacterium *Escherichia coli* as described in Example 4. The treatments were performed with four parallels.

Results and Discussion

Gram-positive bacteria are generally considered to be more susceptible to photodynamic therapy than Gram-negative bacteria. Therefore, *S. epidermidis* was incubated for 10 min (37° C.), irradiated with blue light for 10 min (9.5 J/cm$^2$) and incubated again for 10 min while *K. pneumoniae* and *P. aeruginosa* were incubated for 30 min (37° C.), irradiated with blue light for 30 min (27 J/cm$^2$) and incubated again for 30 min.

The citric acid solution diluted 1:200 with PBS was highly toxic to *S. epidermidis*, both with and without irradiation with blue light (Table 10). A similar toxic effect was observed with NADES 3 at a similar dilution in PBS. The pH neutral NADES 26 was not toxic at this dilution. Therefore, the phototoxic effect of the porphyrin in this NADES at this dilution should be ascribed to a synergistic effect between the NADES and the photosensitiser. NADES 3 was not toxic to *S. epidermidis* at dilution 1:400 in PBS.

The neutral porphyrin THPP at 1 nM was highly phototoxic to *S. epidermidis* in PBS, citric acid solution and NADES 3 diluted 1:400 with PBS (Table 10). Interestingly, the PBS preparation and the citric acid preparation containing 1 nM THPP were approximately equally phototoxic (not significantly different, p>0.05), while the NADES preparation was significantly more phototoxic than both (p<0.05; Table 2). This bacterium was equally or more susceptible to neutral than cationic porphyrins. In the acidic NADES preparation, even though THPP probably was protonated, the presence of the NADES increased the phototoxicity of THPP. THPP (1 nM) in NADES 3 was also toxic in the absence of light (Table 10). This effect was not seen in the citric acid solution, and demonstrated the "NADES effect" on THPP. The NADES itself at this dilution was neither dark toxic nor phototoxic to *S. epidermidis*. Increasing the THPP concentration to 5 nM resulted in complete photoinactivation of *S. epidermidis* in all three solvents (results not shown). Thus, *S. epidermidis* and *E. faecalis* (Example 1) are equally sensitive to photodynamic treatment with THPP in NADES 3 (also named CS).

A similar trend was observed for the cationic porphyrin TMAP. TMAP (1 nM) in PBS or citric acid solution was not phototoxic or dark toxic to *S. epidermidis* while the same concentration of TMAP in the pH-neutral NADES 26 was phototoxic (Table 10). This is due to the synergistic antibacterial effect between the NADES and the porphyrin as pure NADES 26 (diluted 1:200) was non-toxic to *S. epidermidis* (Table 10). Increasing the concentration of TMAP to 5 nM increased the phototoxicity of TMAP in all three solutions, but did not result in complete photoinactivation of *S. epidermidis*. Thus, *S. epidermidis* is more tolerant to TMAP in NADES 26 than *E. faecalis* and *S. aureus* (Example 5).

TABLE 10

Percent viable colony forming units per ml (±SD) of *S. epidermidis* after treatment with diluted NADES, diluted individual NADES components, and THPP and TMAP in various preparations with 9.5 J/cm$^2$ blue light or no irradiation (n = 4).

| Sample (*S. epidermidis*) | Dilution | % survival (9.5 J/cm$^2$) | % survival (dark) |
|---|---|---|---|
| Citric acid | 1:200 | 0.1 ± 0.0 | 0.7 ± 0.3 |
| Choline chloride | 1:200 | 124 ± 7 | 104 ± 12 |
| Xylitol | 1:200 | 118 ± 12 | 98 ± 10 |
| Sucrose | 1:200 | 134 ± 14 | 113 ± 5 |
| NADES 3 | 1:200 | 0.0 ± 0.0 | 0.2 ± 0.1 |
| NADES 26 | 1:200 | 129 ± 9 | 106 ± 5 |
| 1 nM THPP in PBS | 1:200 | 0.6 ± 0.1 | 115 ± 9 |
| 1 nM THPP in citric acid | 1:400 | 0.9 ± 0.2 | 101 ± 10 |
| 1 nM THPP in NADES 3 | 1:400 | 0.1 ± 0.1 | 8 ± 2 |
| 1 nM TMAP in PBS | 1:200 | 121 ± 14 | 115 ± 12 |
| 1 nM TMAP in citric acid | 1:400 | 99 ± 4 | 91 ± 6 |
| 1 nM TMAP in NADES 26 | 1:200 | 63 ± 6 | 108 ± 4 |

The acidic NADES 3 and NADES 35 were much more toxic than the individual NADES components at the same concentrations and dilutions on *K. pneumoniae* (Table 11). The NADES were diluted 1:200 in these studies and yet they resulted in complete photoinactivation of *K. pneumoniae* (Table 11). The same NADES were also extremely toxic to the bacterium at no dilution.

Low concentrations that would not result in complete eradication of the bacteria were selected to visualise the differences in phototoxicity of the porphyrins in PBS (pH 7.4), citric acid solution (pH ~4) and in NADES (pH 4-5). THPP (20 nM) in PBS resulted in 49% reduction in the viable amount of *K. pneumonia* after treatment with 27 J/cm$^2$ blue light (Table 11). THPP in citric acid solution, with a pH that resulted in protonation of the porphyrin nitrogens, increased the phototoxic potential of THPP and resulted in 12% survival (Table 11). THPP in NADES 3 was the most phototoxic combination (Table 11). The pH in this NADES after dilution 1:400 with PBS was approximately the same as in the citric acid solution. Therefore, the increase in phototoxicity of THPP on this bacterium was a result of the "NADES effect" rather than just protonation of the porphyrin. *K. pneumoniae* appeared to tolerate the photodynamic treatment with THPP in NADES 3 slightly better than *E. coli* (see Example 1) on which 5 nM THPP in NADES 3 resulted in complete photoinactivation.

Similar results were obtained for the cationic porphyrin TMAP. Even though TMAP already was protonated in PBS, 1-5 nM TMAP in PBS was not significantly phototoxic to *K. pneumonia* (p>0.05; Table 3). However, the phototoxicity increased after protonation of the porphyrin nitrogens in citric acid solution, and even more in NADES 35 (even after dilution 1:800 so that the NADES itself would not be toxic; Table 11). It was seen that NADES 35 at dilution 1:800 was neither phototoxic nor dark toxic to *K. pneumonia*. However, upon the addition of 5 nM TMAP, the preparation was highly dark toxic as well as phototoxic (Table 11). This effect was not seen in simple citric acid, indicating that there was a synergistic toxic effect between the NADES and TMAP. The phototoxicity of TMAP prepared in NADES 35 on *K. pneumoniae* was comparable to the phototoxicity of this preparation on *E. coli* (see Example 5).

TABLE 11

Percent viable colony forming units per ml (±SD) of *K. pneumoniae* after treatment with diluted NADES, diluted individual NADES components, and THPP and TMAP in various preparations with 27 J/cm$^2$ blue light or no irradiation (n = 4).

| Sample (*K. pneumonia*) | Dilution | % survival (27 J/cm$^2$) | % survival (dark) |
|---|---|---|---|
| Citric acid | 1:200 | 145 ± 2 | 38 ± 18 |
| Xylitol | 1:200 | 74 ± 17 | 72 ± 19 |
| Sucrose | 1:200 | 84 ± 18 | 124 ± 9 |
| NADES 3 | 1:200 | 0.0 ± 0.0 | 0.0 ± 0.0 |
| NADES 35 | 1:200 | 0.0 ± 0.0 | 0.0 ± 0.0 |
| 20 nM THPP in PBS | 1:200 | 49 ± 22 | 97 ± 10 |
| 20 nM THPP in citric acid | 1:400 | 12 ± 3 | 82 ± 24 |
| 20 nM THPP in NADES 3 | 1:400 | 3 ± 1 | 95 ± 15 |
| 1 nM TMAP in PBS | 1:200 | 80 ± 19 | 95 ± 13 |
| 1 nM TMAP in citric acid | 1:400 | 10 ± 7 | 75 ± 11 |
| 1 nM TMAP in NADES 35 | 1:800 | 0.5 ± 0.4 | 88 ± 19 |
| 5 nM TMAP in PBS | 1:200 | 110 ± 2 | 79 ± 15 |
| 5 nM TMAP in citric acid | 1:400 | 0.8 ± 0.6 | 73 ± 7 |
| 5 nM TMAP in NADES 35 | 1:800 | 0.0 ± 0.0 | 0.0 ± 0.0 |

NADES 3 was slightly, though significantly more phototoxic than the citric acid solution at similar concentrations and dilutions on *P. aeruginosa* (p<0.05; Table 12). NADES 3 was also significantly (p<0.05) more dark toxic at dilution 1:400 than the citric acid solution at the similar dilution (Table 12). NADES 35 resulted in no viable bacteria upon dilution <1:800 with PBS, and was more phototoxic than dark toxic (Table 12). The individual components of NADES 35, citric acid and xylitol, were not toxic at all at dilution 1:800. The results emphasise that NADES on *P. aeruginosa* possessed an antibacterial effect even at very high dilutions which could be potentiated through irradiation with blue light.

Protonation of the porphyrin THPP in citric acid solution and NADES 3 enhanced the phototoxicity compared to a solution in PBS (Table 12). Even though the citric acid solution at dilution 1:800 was not toxic to *P. aeruginosa*, 5 nM THPP was very phototoxic and somewhat dark toxic in a solution of 1:800 citric acid or NADES 3 (Table 12). *P. aeruginosa* appeared to be just as sensitive to THPP prepared in NADES 3 as *E. coli* was, but even more sensitive to acidic solutions (see Example 1 and 4). A similar observation was made with the cationic porphyrin TMAP. This porphyrin was not phototoxic at 1 nM or 5 nM in PBS, possibly due to neutralisation of the cationic charges by chloride ions in the buffer. In citric acid solution (diluted 1:800 with PBS not to be toxic in itself) or NADES 35 (diluted 1:1600 with PBS not to be toxic in itself) even 1 nM TMAP resulted in almost complete eradication of *P. aeruginosa* both with and without irradiation with blue light (Table 12). The pH in NADES 35 diluted 1:1600 with PBS was slightly higher than in the citric acid solution diluted 1:800 times, making it useful for topical application on an infection. Further, a NADES preparation of the porphyrin is suitable as a drug product due to increased viscosity, ease of application and increased storage stability of TMAP relative to a simple acidic solution in water.

TABLE 12

Percent viable of colony forming units per ml (±SD) of P. aeruginosa after treatment with diluted NADES, diluted individual NADES components, and THPP and TMAP in various preparations with 27 J/cm² blue light or no irradiation (n = 4).

| Sample (P. aeruginosa) | Dilution | % survival (27 J/cm²) | % survival (dark) |
|---|---|---|---|
| Citric acid | 1:400 | 6 ± 2 | 37 ± 9 |
| Xylitol | 1:200 | 143 ± 17 | 140 ± 19 |
| Sucrose | 1:200 | 98 ± 19 | 204 ± 22 |
| NADES 3 | 1:400 | 2 ± 1 | 9 ± 5 |
| NADES 35 | 1:800 | 4 ± 1 | 52 ± 9 |
| 5 nM THPP in PBS | 1:200 | 80 ± 5 | 143 ± 15 |
| 5 nM THPP in citric acid | 1:800 | 0.8 ± 0.3 | 66 ± 24 |
| 5 nM THPP in NADES 3 | 1:800 | 0.6 ± 0.1 | 93 ± 20 |
| 1 nM TMAP in PBS | 1:200 | 113 ± 3 | 144 ± 32 |
| 1 nM TMAP in citric acid | 1:800 | 0.8 ± 0.2 | 0.9 ± 0.0 |
| 1 nM TMAP in NADES 35 | 1:1600 | 0.8 ± 0.1 | 1.0 ± 0.2 |

Conclusion

The different Gram-positive and Gram-negative bacteria had different tolerance to aPDT with porphyrins and NADES. In all cases in this study the NADES potentiated the phototoxic effect of the porphyrin, sometimes also by increasing the dark toxicity of the formulation while none of the individual components were toxic to the bacteria. NADES 3 and NADES 35 at dilution 1:200 with PBS were highly toxic to K. pneumoniae both with and without irradiation with blue light, even though their individual components were not toxic. Therefore, they were diluted ≥1:400 to eliminate the "background" antibacterial effect. The pure NADES was more antibacterial than their individual components on P. aeruginosa as well. Thus, the investigated NADES have an antibacterial effect on both the Gram-negative bacteria studied.

The neutral porphyrin THPP was the most phototoxic to S. epidermidis while the cationic porphyrin TMAP was the most phototoxic to the Gram-negative bacteria K. pneumoniae and P. aeruginosa.

Example 8

Antifungal Effect of Natural Deep Eutectic Solvents (NADES) with and without Porphyrins on Candida albicans Introduction The antibacterial effect of natural deep eutectic solvents (NADES) has been demonstrated on Gram-positive and Gram-negative bacteria (Examples 3 and 4). Enhancement of the antibacterial effect by combination with blue light (phototoxic effect) of NADES prepared both with and without a photosensitiser has also been demonstrated on bacteria (Examples 1-7).

Previous studies have shown that Gram-negative bacteria are more difficult to eradicate with antimicrobial photodynamic therapy (aPDT) than Gram-positive bacteria, and that yeasts are even harder to eradicate with aPDT than Gram-negative bacteria. This is, in part, due to their size as they are typically ten times larger than bacteria (3-40 µm).

Porphyrins exert their phototoxic effect in PDT primarily by the photoinduced formation of singlet oxygen which can be lethal to cells and bacteria if the concentration is high enough. Singlet oxygen is very reactive and has a short lifetime in aqueous solution (a few microseconds) which corresponds to a short diffusion distance of 10-100 nm depending on nearby reactive molecules. It is therefore contemplated that more singlet oxygen is needed to kill yeast cells than bacteria.

This example describes the antifungal and phototoxic effect of two selected acidic NADES (NADES 3 and NADES 35) and two pH-neutral NADES (NADES 26 and NADES 39) on Candida albicans. The phototoxic potential of tetra-hydroxyphenyl-porphyrin (THPP) and tetra-(4-trimethylanilinum)-porphine tetrachloride (TMAP) in different solutions was also investigated.

Materials and Methods

Preparation of the Samples

The NADES were prepared as previously described (see Example 1). Briefly, the components of each NADES (see Table 13) were mixed and dissolved in a round flask with 50 ml of warm water (~50° C.) before evaporation of the solvent at 45° C. for 15 min with a rotatory evaporator. The pure NADES 3, NADES 26, NADES 35 and NADES 39 were mixed undiluted or after dilution 1:50 with phosphate buffered saline (PBS, Lonza, Verviers, Belgium) with the yeast suspension (1:1) in the toxicity studies.

TMAP and THPP (Frontier Scientific, Inc., Logan, Utah, USA) were prepared in PBS, a 6.8 mM citric acid solution or in NADES as described in Example 7. THPP in NADES 26 was also prepared by dilution of THPP in NADES 3 750 times with pure NADES 26 to give a final concentration of 40 nM THPP in NADES 26. This solution was mixed 1:1 with the yeast suspension in the phototoxicity studies resulting in 20 nM THPP.

Aqueous solutions of 2.7 M citric acid, 2.1 M fructose, 2.3 M xylitol, 2.5 M sucrose and 5 M choline chloride were used to investigate the toxicity of the individual compounds of the NADES. The concentrations of the excipients were the same as in the respective NADES after evaporation of unbound water. The solutions were diluted totally 1:1 or 1:100 with PBS and yeast suspension in the toxicity studies.

TABLE 13

The molar ratio and components of each natural deep eutectic solvent investigated.

| NADES no. | Molar ratio | Component 1 | Component 2 |
|---|---|---|---|
| 3 | 1:1 | Citric acid | Sucrose |
| 26 | 5:2 | Choline chloride | Xylitol |
| 35 | 1:1 | Citric acid | Xylitol |
| 39 | 5:2 | Choline chloride | D-(−)-fructose |

Toxicity Studies

Toxicity studies were performed as described in Example 4. The studies were performed on C. albicans (ATCC CRM-10231) which was re-suspended from glycerol at −20° C. in glucose-yeast-peptone medium and incubated at 30° C. for 24 h. The overnight cultures were centrifuged (4000 g, 22° C., 10 min), the medium replaced and diluted with PBS to $OD_{600}$ 0.1. The plates containing C. albicans samples were treated similarly to the Gram-negative bacteria (Example 4), i.e. incubation for 30 min (30° C.), irradiation with blue light for 30 min (corresponding to 27 J/cm²±10%) and incubation again for 30 min (30° C.).

Results and Discussion

No significant reduction in viable C. albicans was observed after incubation in the dark or after light treatment with 2.1 M fructose, 2.3 M xylitol, 2.5 M sucrose and 5 M choline chloride diluted 1:1 or 1:100 in the toxicity studies (p>0.05; FIG. 1). Citric acid (2.7 M) diluted 1:1 did however result in a 73±8% reduction in viable *C. albicans* after light treatment and a slight, though significant, reduction after incubation in the dark. The antifungal effect observed with NADES 3 was, however, significantly higher than the toxicity from the citric acid component at a similar concentration. NADES 3 and NADES 35 were even phototoxic to *C. albicans* after a total dilution of 1:100. None of the individual components of these NADES resulted in a similar reduction in viable *C. albicans* after light or dark treatment. Therefore, the antifungal effect can be ascribed to the NADES.

Similar results were obtained for all the investigated NADES, e.g., similar phototoxicity and antifungal effect when they were used undiluted and mixed 1:1 with the yeast suspension. No obvious difference in *C. albicans* sensitivity was observed for the pH-neutral NADES and the acidic NADES. The NADES possessed a higher antifungal effect after incubation in the dark than any of the individual components of each NADES. Upon irradiation with blue light, the antifungal effect of the NADES increased. The treatment with NADES 39 mixed 1:1 with the *C. albicans* suspension resulted in complete eradication of the yeast both with and without irradiation with blue light. Upon dilution of this NADES 1:100 with PBS much or all of the native antifungal and phototoxic effect towards *C. albicans* was lost.

TMAP (20 nM) prepared in PBS, in a citric acid solution or in NADES 35 was not toxic to *C. albicans*, neither with nor without the combination with blue light. THPP (20 nM) prepared in a citric acid solution or in NADES 3 did not possess any antifungal effect towards *C. albicans* (with or without blue light). THPP (20 nM) in PBS, however, resulted in a 73±20% reduction in viable *C. albicans*. It was contemplated that *C. albicans* was less tolerant to neutral photosensitisers in a neutral environment (e.g., THPP in NADES 26) than to charged photosensitisers. As THPP was poorly soluble in the pH-neutral NADES 26 when added directly to the solvent, the solution of THPP (20 nM) in the acidic NADES 3 was diluted 750 times with pure NADES 26 to obtain a solution of THPP in NADES 26. THPP remained soluble in this pH-neutral preparation for the desired period of treatment (1.5 h). As postulated, 20 nM THPP in NADES 26 mixed 1:1 with the yeast suspension resulted in a complete photoinactivation of *C. albicans*. Without the combination with blue light 58±15% CFU/ml survived the treatment, similar to what was observed for pure NADES 26. This study on THPP demonstrated that the phototoxic effect of the NADES towards *C. albicans* was increased upon dissolution of a neutral photosensitiser in a neutral NADES. Compared to the solution of 20 nM THPP in PBS it is evident that NADES 26 also increased the phototoxic effect of THPP.

The THPP concentration in NADES needed for complete eradication of *C. albicans* is comparable to the porphyrin concentration needed to photoinactivate Gram-negative bacteria (Examples 1, 5-7). This was observed even though yeasts typically are ten times larger than bacteria, which should result in higher tolerance for small toxic molecules like singlet oxygen. The results indicate that the NADES weakened the cell wall of the yeast. This brought the photosensitiser in close contact with vital parts of the cell inducing lethal cell damage upon irradiation and thereby production of toxic singlet oxygen.

Conclusion

The pure NADES possessed an antifungal effect towards *C. albicans*, which was increased with the combination with blue light. This demonstrated that the pure NADES can be used to treat local infections that involve not only bacteria, as previously reported (Examples 3 and 4), but also the common yeast *C. albicans*. The pH-neutral NADES 39 was the most effective NADES and eradicated *C. albicans* completely under the investigated experimental conditions.

The cationic porphyrin TMAP was not phototoxic towards *C. albicans* in any of the preparations. The neutral porphyrin THPP was phototoxic in pH-neutral PBS and in the pH-neutral NADES 26. The NADES 26-preparation of THPP resulted in complete photoinactivation of *C. albicans*. That the addition of THPP to NADES 26 resulted in increased phototoxicity compared to the pure NADES showed that this was an even more effective antifungal treatment than NADES alone. The NADES potentiated the phototoxicity of THPP compared to in PBS. The results correspond well with the general understanding that yeasts are even more difficult to kill with PDT than Gram-negative bacteria. It was also confirmed that a neutral photosensitiser in a neutral NADES is the potentially most phototoxic preparation towards *C. albicans*.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method of killing or inhibiting the growth of a bacterial cell, fungal cell, or cancer cell, comprising:
    contacting said cell with a composition comprising a eutectic solvent and a photosensitizer selected from the group consisting of a porphyrin compround, a chlorin compound, a bacteriochlorin compound, a phthalocyanine compound, a texaphyrin comppund, a sapphyrin compound a porphycene compound, a curcuminoid compound, and a flavin compound.

2. A composition comprising a eutectic solvent and a photosensitizer selected from the group consisting of a porphyrin compround, a chlorin compound, a bacteriochlorin compound, a phthalocyanine compound a texaphyrin compound, a sapphyrin compound, a porphycene compound, a curcuminoid compound, and a flavin compound.

3. The composition of claim 2, wherein said eutectic solvent is selected from the group consisting of a deep eutectic solvent (DES) and a natural deep eutectic solvent (NADES).

4. The composition of claim 2, wherein said eutectic solvent comprises at least two components selected from the group consisting of an organic acid, a salt, a sugar, a sugar alcohol, an amino acid, a di or tri alkanol, and a choline derivative.

5. The composition of claim 4, wherein said choline derivative is choline or phosphatidylcholine.

6. The composition of claim 4, wherein said sugar or sugar alcohol is selected from the group consisting of sucrose, glucose, fructose, lactose, maltose, cellobiose, arabinose, ribose, ribulose, galactose, rhamnose, raffinose, xylose, sucrose, mannose, trehalose, mannitol, sorbitol, inositol, ribitol, galactitol, erythritol, xylitol and adonitol, and a phosphate thereof.

7. The composition of claim 4, wherein said organic acid is selected from malic acid, maleic acid, citric acid, lactic acid, pyruvic acid, fumaric acid, succinic acid, lactic acid, acetic acid, aconitic acid, tartaric acid, malonic acid, ascorbic acid, glucuronic acid, oxalic acid, neuraminic acid and sialic acids.

8. The composition of claim 4, wherein the first component is selected from the group consisting of citric acid, choline chloride, D-(+)-glucose, and sucrose.

9. The composition of claim 8, wherein the second component is selected from the group consisting of sucrose, D-(+)-trehalose, choline chloride, DL-malic acid, glycerol, sucrose, xylitol and D-(−)-fructose.

10. The composition of claim 8, wherein said eutectic solvent comprises said first and second components at a molar ratio of 1:1, 1:2, 1:3, 1:4, 1:5, 2:1, 2:3, 2:4, 2:5, 3:1, 3:2, 3:4, 3:5, 4:1, 4:2, 4:3, 4:5, 5:1, 5:2, 5:3, or 5:4.

11. The composition of claim 2, wherein said eutectic solvent comprises an organic acid and a sugar or sugar alcohol in a molar ratio characteristic of formation of eutectic solution by said organic acid and a sugar or sugar alcohol.

12. The composition of claim 2, wherein said eutectic solvent comprises a choline salt and a sugar, sugar alcohol, or organic acid in a molar ratio consistent with formation of eutectic solution by said organic acid and a sugar or sugar alcohol.

13. The composition of claim 2, wherein said eutectic solvent comprises at least two sugars or sugar alcohols in a molar ratio consistent with formation of eutectic solution by said at least two sugars or sugar alcohols.

14. The composition of claim 2, wherein said eutectic solvent comprises at least three sugars or sugar alcohols or organic acids in a molar ratio consistent with formation of eutectic solution by said at least two sugars or sugar alcohols.

15. The composition of claim 2, wherein said eutectic solvent is selected from the group consisting of citric acid and sucrose at a molar ratio of 1:1, choline chloride and maleic acid at a molar ratio of 1:1, choline chloride and glycerol at a molar ration of 1:1, D-(+)-glucose and DL-malic acid at a molar ratio of 1:1, choline chloride and citric acid at a molar ratio of 2:1, citric acid and xylitol at a molar ratio of 1:1, choline chloride and xylitol at a molar ratio of 5:2, choline chloride and D-(−)-fructose at a molar ratio of 5:2, choline chloride and maleic acid 2:1, choline chloride and maleic acid 1:3, and glucose and sucrose 1:1.

16. The composition of claim 2, wherein said eutectic solvent comprises sucrose, glucose, and fructose at a ratio of 1:1:1, or DL-malic acid and D-(−)-fructose and D-(+)-glucose at a molar ratio 1:1:1.

17. The composition of claim 2, wherein said eutectic solvent is provided in a solution comprising a 1:1 to 1:1000 dilution of said eutectic solvent in water or an aqueous buffer.

18. The composition of claim 2, wherein said porphyrin is 5,10,15,20-tetrakis(4-hydroxyphenyl)porphyrin (THPP), tetra-(4-trimethylanilinum)-porphine tetrachloride (TMAP), or porphyrin tetra-(4-carboxyphenyl)-porphine (TCPP).

19. The composition of claim 2, wherein said curcuminoid is curcumin.

* * * * *